US010183042B2

(12) United States Patent
Leach et al.

(10) Patent No.: US 10,183,042 B2
(45) Date of Patent: *Jan. 22, 2019

(54) APPARATUS AND METHOD FOR SEPARATING AND CONCENTRATING FLUIDS CONTAINING MULTIPLE COMPONENTS

(71) Applicant: Biomet Manufacturing, LLC

(72) Inventors: Michael D. Leach, Warsaw, IN (US); Joel C. Higgins, Claypool, IN (US); Matthew Swift, Fort Wayne, IN (US); Nathan Gordon, Plymouth, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 643 days.

This patent is subject to a terminal disclaimer.

(21) Appl. No.: 14/461,845

(22) Filed: Aug. 18, 2014

(65) Prior Publication Data
US 2014/0356446 A1 Dec. 4, 2014

Related U.S. Application Data

(60) Continuation of application No. 12/946,338, filed on Nov. 15, 2010, now Pat. No. 8,808,551, which is a
(Continued)

(51) Int. Cl.
*A61M 1/36* (2006.01)
*B01L 3/00* (2006.01)
(Continued)

(52) U.S. Cl.
CPC ........... *A61K 35/12* (2013.01); *A61M 1/3693* (2013.01); *B01L 3/502* (2013.01); *B01L 3/5021* (2013.01);
(Continued)

(58) Field of Classification Search
CPC .. A61K 35/12; A61M 1/3693; B01L 3/50215; B01L 3/502; B01L 3/5021;
(Continued)

(56) References Cited

U.S. PATENT DOCUMENTS

| 280,820 A | 7/1883 | Hickson et al. |
| 593,333 A | 11/1897 | Park |

(Continued)

FOREIGN PATENT DOCUMENTS

| AU | 696278 | 1/1999 |
| BR | 9103724 | 3/1993 |

(Continued)

OTHER PUBLICATIONS

International Preliminary Report on Patentability and Written Opinion dated Mar. 12, 2015 for PCT/US2013/056793 claiming benefit of U.S. Appl. No. 13/595,461, filed Aug. 27, 2012.
(Continued)

*Primary Examiner* — David C Mellon
(74) *Attorney, Agent, or Firm* — Schwegman Lundberg & Woessner, P.A.

(57) ABSTRACT

An apparatus may allow separating and collecting a fraction of a sample. The apparatus, when used with a centrifuge, allows for the creation of at least three fractions in the apparatus. It also provides for a new method of extracting the buffy coat phase from a whole blood sample and mesenchymal stem cells from bone reaming material. A buoy system that may include a first buoy portion and a second buoy member operably interconnected may be used to form at least three fractions from a sample during a substantially single centrifugation process. Therefore, the separation of various fractions may be substantially quick and efficient.

23 Claims, 8 Drawing Sheets

Related U.S. Application Data division of application No. 11/441,275, filed on May 25, 2006, now Pat. No. 7,832,566, which is a continuation-in-part of application No. 10/932,882, filed on Sep. 2, 2004, now Pat. No. 7,374,678, which is a continuation-in-part of application No. 10/445,381, filed on May 23, 2003, now Pat. No. 7,179,391.

(60) Provisional application No. 60/383,013, filed on May 24, 2002.

(51) Int. Cl.
    *B01L 9/00*         (2006.01)
    *A61K 35/12*       (2015.01)
    *G01N 33/49*      (2006.01)

(52) U.S. Cl.
CPC ........ *B01L 3/50215* (2013.01); *G01N 33/491* (2013.01); *B01L 9/54* (2013.01); *B01L 2200/026* (2013.01); *B01L 2300/0681* (2013.01); *B01L 2400/0409* (2013.01); *B01L 2400/0478* (2013.01); *B01L 2400/0605* (2013.01)

(58) Field of Classification Search
CPC ..... B01L 2400/0409; B01L 2300/0681; B01L 2400/0605; B01L 2400/0478; B01L 2200/026; B01L 9/54; G01N 33/491
See application file for complete search history.

(56) References Cited

U.S. PATENT DOCUMENTS

| | | |
|---|---|---|
| 1,468,313 A | 9/1923 | Lux |
| 1,593,814 A | 7/1926 | Vogel |
| 2,722,257 A | 11/1955 | Lockhart |
| 3,013,557 A | 12/1961 | Pallotta |
| 3,141,846 A | 7/1964 | Laven, Jr. |
| 3,159,159 A | 12/1964 | Cohen |
| 3,300,051 A | 1/1967 | Mitchell |
| 3,409,165 A | 11/1968 | Creith |
| 3,420,374 A | 1/1969 | Umeda |
| 3,441,143 A | 4/1969 | Kudlaty |
| 3,453,364 A | 7/1969 | Flodin et al. |
| 3,469,369 A | 9/1969 | Helmke |
| 3,508,653 A | 4/1970 | Coleman |
| 3,545,671 A | 12/1970 | Ross |
| 3,583,627 A | 6/1971 | Wilson |
| 3,596,652 A | 8/1971 | Winkelman |
| 3,647,070 A | 3/1972 | Adler |
| 3,654,925 A | 4/1972 | Holderith |
| 3,661,265 A | 5/1972 | Greenspan |
| 3,706,305 A | 12/1972 | Berger et al. |
| 3,706,306 A | 12/1972 | Berger et al. |
| 3,723,244 A | 3/1973 | Breillatt, Jr. |
| 3,741,400 A | 6/1973 | Dick |
| 3,779,383 A | 12/1973 | Ayres |
| 3,785,549 A | 1/1974 | Latham, Jr. |
| 3,814,248 A | 6/1974 | Lawhead |
| 3,849,072 A | 11/1974 | Ayres |
| 3,850,369 A | 11/1974 | Bull et al. |
| 3,879,295 A | 4/1975 | Glover et al. |
| 3,887,466 A | 6/1975 | Ayres |
| 3,894,952 A | 7/1975 | Ayres |
| 3,896,733 A | 7/1975 | Rosenberg |
| 3,897,337 A | 7/1975 | Ayres |
| 3,897,343 A | 7/1975 | Ayres |
| 3,909,419 A | 9/1975 | Ayres |
| 3,929,646 A | 12/1975 | Adler |
| 3,931,010 A | 1/1976 | Ayres et al. |
| 3,931,018 A | 1/1976 | North, Jr. |
| 3,935,113 A | 1/1976 | Ayres |
| 3,937,211 A | 2/1976 | Merten |
| 3,941,699 A | 3/1976 | Ayres |
| 3,945,928 A | 3/1976 | Ayres |
| 3,951,801 A | 4/1976 | Ayres |
| 3,957,654 A | 5/1976 | Ayres |
| 3,962,085 A | 6/1976 | Liston et al. |
| 3,965,889 A | 6/1976 | Sachs |
| 3,972,812 A | 8/1976 | Gresl, Jr. |
| 3,982,691 A | 9/1976 | Schlutz |
| 4,001,122 A | 1/1977 | Griffin |
| 4,020,831 A | 5/1977 | Adler |
| 4,046,699 A | 9/1977 | Zine, Jr. |
| 4,055,501 A | 10/1977 | Cornell |
| 4,059,108 A | 11/1977 | Latham, Jr. |
| 4,066,549 A | 1/1978 | Oeser et al. |
| 4,077,396 A | 3/1978 | Wardlaw et al. |
| 4,088,582 A | 5/1978 | Murty et al. |
| 4,146,172 A | 3/1979 | Cullis et al. |
| 4,152,270 A | 5/1979 | Cornell |
| 4,154,690 A | 5/1979 | Ballies et al. |
| 4,159,896 A | 7/1979 | Levine et al. |
| 4,187,979 A | 2/1980 | Cullis et al. |
| 4,189,385 A | 2/1980 | Greenspan |
| 4,203,840 A | 5/1980 | Stoeppler et al. |
| 4,204,537 A | 5/1980 | Latham, Jr. |
| 4,225,580 A | 9/1980 | Rothman et al. |
| 4,229,298 A | 10/1980 | Bange |
| 4,269,718 A | 5/1981 | Persidsky |
| 4,294,707 A | 10/1981 | Ikeda et al. |
| 4,298,598 A | 11/1981 | Schwarz et al. |
| 4,300,717 A | 11/1981 | Latham, Jr. |
| 4,303,193 A | 12/1981 | Latham, Jr. |
| 4,314,823 A | 2/1982 | Rich, Jr. et al. |
| 4,322,298 A | 3/1982 | Persidsky |
| 4,332,351 A | 6/1982 | Kellogg et al. |
| 4,362,567 A | 12/1982 | Schwarz et al. |
| 4,364,832 A | 12/1982 | Ballies et al. |
| 4,377,572 A | 3/1983 | Schwarz et al. |
| 4,379,849 A | 4/1983 | Heimreid |
| 4,411,794 A | 10/1983 | Schwinn et al. |
| 4,414,976 A | 11/1983 | Schwarz et al. |
| 4,416,654 A | 11/1983 | Schoendorfer et al. |
| 4,417,981 A | 11/1983 | Nugent |
| 4,424,132 A | 1/1984 | Iriguchi |
| 4,427,650 A | 1/1984 | Stroetmann et al. |
| 4,427,651 A | 1/1984 | Stroetmann et al. |
| 4,442,655 A | 4/1984 | Stroetmann |
| 4,443,345 A | 4/1984 | Wells |
| 4,445,550 A | 5/1984 | Davis et al. |
| 4,446,021 A | 5/1984 | Aufderhaar et al. |
| 4,453,927 A | 6/1984 | Sinko |
| 4,453,939 A | 6/1984 | Zimmerman et al. |
| 4,464,167 A | 8/1984 | Schoendorfer et al. |
| 4,511,662 A | 4/1985 | Baran et al. |
| 4,537,767 A | 8/1985 | Rothman et al. |
| RE32,089 E | 3/1986 | Blatt et al. |
| 4,577,514 A | 3/1986 | Bradley et al. |
| 4,610,656 A | 9/1986 | Mortensen |
| 4,617,009 A | 10/1986 | Ohlin et al. |
| 4,627,879 A | 12/1986 | Rose et al. |
| 4,631,055 A | 12/1986 | Redl et al. |
| 4,632,761 A | 12/1986 | Bowers et al. |
| 4,639,316 A | 1/1987 | Eldgheidy |
| 4,650,678 A | 3/1987 | Fuhge et al. |
| 4,655,211 A | 4/1987 | Sakamoto et al. |
| 4,672,969 A | 6/1987 | Dew |
| 4,675,117 A | 6/1987 | Neumann et al. |
| 4,680,025 A | 7/1987 | Kruger et al. |
| 4,714,457 A | 12/1987 | Alterbaum |
| 4,722,790 A | 2/1988 | Cawley et al. |
| 4,724,317 A | 2/1988 | Brown et al. |
| 4,735,616 A | 4/1988 | Eibl et al. |
| 4,735,726 A | 4/1988 | Duggins |
| 4,738,655 A | 4/1988 | Brimhall et al. |
| 4,755,300 A | 7/1988 | Fischel et al. |
| 4,755,301 A | 7/1988 | Bowers |
| 4,770,779 A | 9/1988 | Ichikawa et al. |
| 4,776,964 A | 10/1988 | Schoendorfer et al. |
| 4,818,291 A | 4/1989 | Iwatsuki et al. |
| 4,818,386 A | 4/1989 | Burns |
| 4,828,710 A | 5/1989 | Itoh et al. |

(56) References Cited

U.S. PATENT DOCUMENTS

| | | |
|---|---|---|
| 4,832,851 A | 5/1989 | Bowers et al. |
| 4,834,890 A | 5/1989 | Brown et al. |
| 4,839,058 A | 6/1989 | Cawley et al. |
| 4,844,818 A | 7/1989 | Smith |
| 4,846,780 A | 7/1989 | Galloway et al. |
| 4,846,835 A | 7/1989 | Grande |
| 4,850,952 A | 7/1989 | Figdor et al. |
| 4,853,137 A | 8/1989 | Ersson |
| 4,871,462 A | 10/1989 | Fischel et al. |
| 4,874,368 A | 10/1989 | Miller et al. |
| 4,877,520 A | 10/1989 | Burns |
| 4,879,031 A | 11/1989 | Panzani et al. |
| 4,900,453 A | 2/1990 | Sedlmayer et al. |
| 4,902,281 A | 2/1990 | Avoy |
| 4,909,251 A | 3/1990 | Seelich |
| 4,915,847 A | 4/1990 | Dillon et al. |
| 4,917,801 A | 4/1990 | Luderer et al. |
| 4,928,603 A | 5/1990 | Rose et al. |
| 4,929,242 A | 5/1990 | Desecki et al. |
| 4,933,291 A | 6/1990 | Daiss et al. |
| 4,939,081 A | 7/1990 | Figdor et al. |
| 4,943,273 A | 7/1990 | Pages et al. |
| 4,946,601 A | 8/1990 | Fiehler |
| 4,950,220 A | 8/1990 | Wells et al. |
| 4,957,637 A | 9/1990 | Cornell |
| 4,957,638 A | 9/1990 | Smith |
| 4,973,168 A | 11/1990 | Chan |
| 4,983,157 A | 1/1991 | Pober et al. |
| 4,983,158 A | 1/1991 | Headley |
| 4,985,153 A | 1/1991 | Kuroda et al. |
| 5,000,970 A | 3/1991 | Shanbhag et al. |
| 5,002,571 A | 3/1991 | O'Donnell, Jr. et al. |
| 5,019,243 A | 5/1991 | McEwen et al. |
| 5,024,613 A | 6/1991 | Vasconcellos et al. |
| 5,030,215 A | 7/1991 | Morse et al. |
| 5,030,341 A | 7/1991 | McEwen et al. |
| 5,039,401 A | 8/1991 | Columbus et al. |
| 5,045,048 A | 9/1991 | Kaleskas et al. |
| 5,047,004 A | 9/1991 | Wells |
| 5,053,127 A | 10/1991 | Schoendorfer et al. |
| 5,053,134 A | 10/1991 | Luderer et al. |
| 5,071,570 A | 12/1991 | Shiraki et al. |
| 5,080,262 A | 1/1992 | Herold et al. |
| 5,086,784 A | 2/1992 | Levine et al. |
| 5,100,564 A | 3/1992 | Pall et al. |
| 5,104,375 A | 4/1992 | Wolf et al. |
| 5,112,484 A | 5/1992 | Zuk, Jr. |
| 5,112,490 A | 5/1992 | Turpen |
| 5,131,907 A | 7/1992 | Williams et al. |
| 5,137,832 A | 8/1992 | Levine et al. |
| 5,141,645 A | 8/1992 | Shiraki et al. |
| 5,147,290 A | 9/1992 | Jonsson et al. |
| 5,152,905 A | 10/1992 | Pall et al. |
| 5,156,613 A | 10/1992 | Sawyer |
| 5,165,938 A | 11/1992 | Knighton |
| 5,171,456 A | 12/1992 | Hwang et al. |
| 5,173,295 A | 12/1992 | Wehling et al. |
| 5,178,602 A | 1/1993 | Wells |
| 5,185,001 A | 2/1993 | Galanakis |
| 5,188,583 A | 2/1993 | Guigan et al. |
| 5,190,057 A | 3/1993 | Sarfarazi |
| 5,190,759 A | 3/1993 | Lindblad et al. |
| 5,197,985 A | 3/1993 | Caplan et al. |
| 5,203,825 A | 4/1993 | Haynes et al. |
| 5,204,537 A | 4/1993 | Bennet et al. |
| 5,206,023 A | 4/1993 | Hunziker |
| 5,207,638 A | 5/1993 | Choksi et al. |
| 5,217,426 A | 6/1993 | Bacehowski et al. |
| 5,217,627 A | 6/1993 | Pall et al. |
| 5,219,328 A | 6/1993 | Morse et al. |
| 5,226,877 A | 7/1993 | Epstein |
| 5,226,914 A | 7/1993 | Caplan et al. |
| 5,234,608 A | 8/1993 | Duff |
| 5,236,604 A | 8/1993 | Fiehler |
| 5,251,786 A | 10/1993 | Sarrine |
| 5,258,126 A | 11/1993 | Pall et al. |
| 5,260,420 A | 11/1993 | Burnouf-Radosevich et al. |
| 5,269,927 A | 12/1993 | Fiehler |
| 5,271,852 A | 12/1993 | Luoma, II |
| 5,279,825 A | 1/1994 | Wehling et al. |
| 5,281,342 A | 1/1994 | Biesel et al. |
| 5,290,552 A | 3/1994 | Sierra et al. |
| 5,290,918 A | 3/1994 | Bui-Khac et al. |
| 5,298,171 A | 3/1994 | Biesel et al. |
| 5,304,372 A | 4/1994 | Michalski et al. |
| 5,316,674 A | 5/1994 | Pall et al. |
| 5,318,524 A | 6/1994 | Morse et al. |
| 5,318,782 A | 6/1994 | Weis-Fogh et al. |
| 5,321,126 A | 6/1994 | van Dommelen et al. |
| 5,322,620 A | 6/1994 | Brown et al. |
| 5,330,974 A | 7/1994 | Pines et al. |
| 5,344,752 A | 9/1994 | Murphy |
| 5,354,483 A | 10/1994 | Furse |
| 5,370,221 A | 12/1994 | Magnusson et al. |
| 5,370,802 A | 12/1994 | Brown |
| 5,372,945 A | 12/1994 | Alchas et al. |
| 5,376,263 A | 12/1994 | Fischel |
| 5,387,187 A | 2/1995 | Fell et al. |
| 5,393,674 A | 2/1995 | Levine et al. |
| 5,395,923 A | 3/1995 | Bui-Khac et al. |
| 5,403,272 A | 4/1995 | Deniega et al. |
| 5,405,607 A | 4/1995 | Epstein |
| 5,409,833 A | 4/1995 | Hu et al. |
| 5,411,885 A | 5/1995 | Marx |
| 5,417,650 A | 5/1995 | Gordon |
| 5,420,250 A | 5/1995 | Lontz |
| 5,443,481 A | 8/1995 | Lee |
| 5,454,958 A | 10/1995 | Fiehler |
| 5,456,693 A | 10/1995 | Conston et al. |
| 5,456,885 A | 10/1995 | Coleman et al. |
| 5,474,687 A | 12/1995 | Van Vlasselaer |
| 5,480,378 A | 1/1996 | Weis-Fogh et al. |
| 5,484,383 A | 1/1996 | Fitch, Jr. et al. |
| 5,486,359 A | 1/1996 | Caplan et al. |
| 5,494,578 A | 2/1996 | Brown et al. |
| 5,494,592 A | 2/1996 | Latham, Jr. et al. |
| 5,501,371 A | 3/1996 | Schwartz-Feldman |
| 5,505,685 A | 4/1996 | Antwiler |
| 5,510,102 A | 4/1996 | Cochrum |
| 5,520,885 A | 5/1996 | Coelho et al. |
| 5,525,477 A | 6/1996 | Hassouna |
| 5,533,518 A | 7/1996 | Vogler |
| 5,560,830 A | 10/1996 | Coleman et al. |
| 5,571,418 A | 11/1996 | Lee et al. |
| 5,575,778 A | 11/1996 | Hardt et al. |
| 5,577,513 A | 11/1996 | Van Vlasselaer |
| 5,585,007 A | 12/1996 | Antanavich et al. |
| 5,588,958 A | 12/1996 | Cunningham et al. |
| 5,589,462 A | 12/1996 | Patat et al. |
| 5,601,711 A | 2/1997 | Sklar et al. |
| 5,601,727 A | 2/1997 | Bormann et al. |
| 5,603,845 A | 2/1997 | Holm |
| 5,607,579 A | 3/1997 | Latham, Jr. et al. |
| 5,614,106 A | 3/1997 | Payrat et al. |
| 5,618,663 A | 4/1997 | Delmas et al. |
| 5,632,895 A | 5/1997 | Tsukagoshi et al. |
| 5,632,905 A | 5/1997 | Haynes |
| 5,641,414 A | 6/1997 | Brown |
| 5,641,622 A | 6/1997 | Lake et al. |
| 5,643,192 A | 7/1997 | Hirsh et al. |
| 5,643,193 A | 7/1997 | Papillon et al. |
| 5,645,540 A | 7/1997 | Henniges et al. |
| 5,646,004 A | 7/1997 | Van Vlasselaer |
| 5,648,223 A | 7/1997 | Van Vlasselaer |
| 5,649,903 A | 7/1997 | Deniega et al. |
| 5,663,051 A | 9/1997 | Vlasselaer |
| 5,674,173 A | 10/1997 | Hlavinka et al. |
| 5,707,331 A | 1/1998 | Wells et al. |
| 5,707,647 A | 1/1998 | Dunn et al. |
| 5,707,876 A | 1/1998 | Levine |
| 5,716,616 A | 2/1998 | Prockop et al. |
| 5,723,331 A | 3/1998 | Tubo et al. |
| 5,724,988 A | 3/1998 | Dennehey et al. |
| 5,733,466 A | 3/1998 | Benebo et al. |

(56) References Cited

U.S. PATENT DOCUMENTS

| | | |
|---|---|---|
| 5,733,545 A | 3/1998 | Hood, III |
| 5,736,033 A | 4/1998 | Coleman et al. |
| 5,738,784 A | 4/1998 | Holm et al. |
| 5,738,796 A | 4/1998 | Bormann et al. |
| 5,750,025 A | 5/1998 | Holmes et al. |
| 5,750,658 A | 5/1998 | Coelho et al. |
| 5,762,798 A | 6/1998 | Wenthold et al. |
| 5,785,700 A | 7/1998 | Olson |
| 5,786,217 A | 7/1998 | Tubo et al. |
| 5,788,662 A | 8/1998 | Antanavich et al. |
| 5,792,344 A | 8/1998 | Holm |
| 5,795,489 A | 8/1998 | Holm et al. |
| 5,795,571 A | 8/1998 | Cederholm-Williams et al. |
| 5,795,751 A | 8/1998 | Apel |
| 5,811,094 A | 9/1998 | Caplan et al. |
| 5,811,151 A | 9/1998 | Hendriks et al. |
| 5,817,519 A | 10/1998 | Zelmanovic et al. |
| 5,823,986 A | 10/1998 | Peterson |
| 5,824,084 A | 10/1998 | Muschler |
| 5,830,359 A | 11/1998 | Knight et al. |
| 5,833,866 A | 11/1998 | Brown |
| 5,834,418 A | 11/1998 | Brazeau et al. |
| 5,837,150 A | 11/1998 | Langley et al. |
| 5,840,502 A | 11/1998 | Van Vlasselaer |
| 5,853,600 A | 12/1998 | McNeal et al. |
| 5,860,937 A | 1/1999 | Cohen |
| 5,863,892 A | 1/1999 | Stern et al. |
| 5,865,785 A | 2/1999 | Bischof |
| 5,885,239 A | 3/1999 | Headley et al. |
| 5,889,584 A | 3/1999 | Wardlaw |
| 5,895,346 A | 4/1999 | Wells et al. |
| 5,899,874 A | 5/1999 | Jonsson et al. |
| 5,900,245 A | 5/1999 | Sawhney et al. |
| 5,906,934 A | 5/1999 | Grande et al. |
| 5,916,557 A | 6/1999 | Berlowitz-Tarrant et al. |
| 5,916,743 A | 6/1999 | Lake et al. |
| 5,918,622 A | 7/1999 | Perez et al. |
| 5,924,972 A | 7/1999 | Turvaville et al. |
| 5,934,803 A | 8/1999 | Hutter |
| 5,938,621 A | 8/1999 | Kelly et al. |
| 5,951,160 A | 9/1999 | Ronk |
| 5,955,032 A | 9/1999 | Kelly et al. |
| 5,955,436 A | 9/1999 | Kunkle, Jr. |
| 5,958,250 A | 9/1999 | Brown et al. |
| 5,958,253 A | 9/1999 | Holm et al. |
| 5,961,210 A | 10/1999 | McCardel et al. |
| 5,980,734 A | 11/1999 | Itoh et al. |
| 5,980,757 A | 11/1999 | Brown et al. |
| 5,985,315 A | 11/1999 | Patat et al. |
| 5,997,544 A | 12/1999 | Nies et al. |
| 5,999,558 A | 12/1999 | Miner, Jr. et al. |
| 6,007,811 A | 12/1999 | Sawyer et al. |
| 6,010,627 A | 1/2000 | Hood, III |
| 6,011,490 A | 1/2000 | Tonnesen et al. |
| 6,020,196 A | 2/2000 | Hu et al. |
| 6,022,306 A | 2/2000 | Dumont et al. |
| 6,025,201 A | 2/2000 | Zelmanovic et al. |
| 6,027,655 A | 2/2000 | Holm |
| 6,049,026 A | 4/2000 | Muschler |
| 6,051,146 A | 4/2000 | Green et al. |
| 6,051,147 A | 4/2000 | Bischof |
| 6,053,856 A | 4/2000 | Hlavinka |
| 6,054,122 A | 4/2000 | MacPhee et al. |
| 6,063,297 A | 5/2000 | Antanavich et al. |
| 6,063,624 A | 5/2000 | Kandler et al. |
| 6,071,421 A | 6/2000 | Brown |
| 6,071,422 A | 6/2000 | Hlavinka et al. |
| 6,071,423 A | 6/2000 | Brown et al. |
| 6,090,793 A | 7/2000 | Zimmermann et al. |
| 6,096,309 A | 8/2000 | Prior et al. |
| 6,102,843 A | 8/2000 | Kelley et al. |
| 6,117,425 A | 9/2000 | MacPhee et al. |
| 6,123,655 A | 9/2000 | Fell et al. |
| 6,150,163 A | 11/2000 | McPherson et al. |
| 6,153,113 A | 11/2000 | Goodrich et al. |
| 6,183,737 B1 | 2/2001 | Zaleske et al. |
| 6,196,987 B1 | 3/2001 | Holmes et al. |
| 6,197,325 B1 | 3/2001 | MacPhee et al. |
| 6,200,287 B1 | 3/2001 | Keller et al. |
| 6,200,606 B1 | 3/2001 | Peterson et al. |
| 6,214,338 B1 | 4/2001 | Antanavich et al. |
| 6,221,315 B1 | 4/2001 | Giesler et al. |
| 6,245,900 B1 | 6/2001 | Yamasaki et al. |
| 6,264,890 B1 | 7/2001 | Boehringer et al. |
| 6,274,090 B1 | 8/2001 | Coelho et al. |
| 6,277,961 B1 | 8/2001 | Hock et al. |
| 6,280,400 B1 | 8/2001 | Niermann |
| 6,286,670 B1 | 9/2001 | Smith |
| 6,296,602 B1 | 10/2001 | Headley |
| 6,316,247 B1 | 11/2001 | Katz et al. |
| 6,322,785 B1 | 11/2001 | Landesberg et al. |
| 6,327,491 B1 | 12/2001 | Franklin et al. |
| 6,328,765 B1 | 12/2001 | Hardwick et al. |
| 6,334,842 B1 | 1/2002 | Hlavinka et al. |
| 6,342,157 B1 | 1/2002 | Hood, III |
| 6,351,659 B1 | 2/2002 | Vilsmeier |
| 6,355,239 B1 | 3/2002 | Bruder et al. |
| 6,368,298 B1 | 4/2002 | Beretta et al. |
| 6,368,498 B1 | 4/2002 | Guilmette |
| 6,398,972 B1 | 6/2002 | Blasetti et al. |
| 6,406,671 B1 | 6/2002 | DiCesare et al. |
| 6,409,528 B1 | 6/2002 | Bodnar |
| 6,410,344 B1 | 6/2002 | Chung et al. |
| 6,417,004 B1 | 7/2002 | Brady et al. |
| 6,432,119 B1 | 8/2002 | Saadat |
| 6,440,444 B2 | 8/2002 | Boyce et al. |
| 6,444,228 B1 | 9/2002 | Baugh et al. |
| 6,464,624 B2 | 10/2002 | Pages |
| 6,471,069 B2 | 10/2002 | Lin et al. |
| 6,472,162 B1 | 10/2002 | Coelho et al. |
| 6,487,992 B1 | 12/2002 | Hollis |
| 6,508,778 B1 | 1/2003 | Verkaart et al. |
| 6,516,953 B1 | 2/2003 | DiCesare et al. |
| 6,523,698 B1 | 2/2003 | Dennehey et al. |
| 6,544,162 B1 | 4/2003 | Van Wie et al. |
| 6,544,727 B1 | 4/2003 | Hei |
| 6,558,341 B1 | 5/2003 | Swisher |
| 6,563,953 B2 | 5/2003 | Lin et al. |
| 6,596,180 B2 | 7/2003 | Baugh et al. |
| 6,623,472 B1 | 9/2003 | Reincke et al. |
| 6,623,959 B2 | 9/2003 | Harris |
| 6,629,919 B2 | 10/2003 | Egozy et al. |
| 6,638,503 B2 | 10/2003 | Chitte et al. |
| 6,676,629 B2 | 1/2004 | Andrew et al. |
| 6,713,246 B1 | 3/2004 | Reinecke et al. |
| 6,716,187 B1 | 4/2004 | Jorgensen et al. |
| 6,719,901 B2 | 4/2004 | Dolecek et al. |
| 6,733,471 B1 | 5/2004 | Ericson et al. |
| 6,758,978 B1 | 7/2004 | Bedell |
| 6,759,188 B2 | 7/2004 | Reinecke et al. |
| 6,764,531 B2 | 7/2004 | Hogan |
| 6,777,231 B1 | 8/2004 | Katz et al. |
| 6,803,022 B2 | 10/2004 | DiCesare et al. |
| 6,811,777 B2 | 11/2004 | Mishra |
| 6,830,762 B2 | 12/2004 | Baugh et al. |
| 6,835,353 B2 | 12/2004 | Smith et al. |
| 6,835,377 B2 | 12/2004 | Goldberg et al. |
| RE38,730 E | 4/2005 | Wells et al. |
| 6,899,813 B2 | 5/2005 | Dolecek et al. |
| 6,905,612 B2 | 6/2005 | Dorian et al. |
| 6,911,202 B2 | 6/2005 | Amir et al. |
| RE38,757 E | 7/2005 | Wells et al. |
| 6,979,307 B2 | 12/2005 | Beretta et al. |
| 7,011,644 B1 | 3/2006 | Andrew et al. |
| 7,077,273 B2 | 7/2006 | Ellsworth et al. |
| 7,077,827 B2 | 7/2006 | Greenfield |
| 7,148,209 B2 | 12/2006 | Hoemann et al. |
| 7,155,288 B2 | 12/2006 | Soykan et al. |
| 7,179,391 B2 | 2/2007 | Leach et al. |
| 7,195,606 B2 | 3/2007 | Ballin |
| 7,223,346 B2 | 5/2007 | Dorian et al. |
| 7,273,886 B2 | 9/2007 | Olivero et al. |
| 7,354,515 B2 | 4/2008 | Coull et al. |
| 7,374,678 B2 | 5/2008 | Leach et al. |

(56) References Cited

U.S. PATENT DOCUMENTS

| | | |
|---|---|---|
| 7,411,006 B2 | 8/2008 | Shanbrom |
| 7,443,346 B2 | 10/2008 | Shih |
| 7,465,293 B2 | 12/2008 | Reinecke et al. |
| 7,470,371 B2 | 12/2008 | Dorian et al. |
| 7,531,355 B2 | 5/2009 | Rodriguez et al. |
| 7,553,413 B2 | 6/2009 | Dorian et al. |
| 7,694,828 B2 | 4/2010 | Swift et al. |
| 7,708,512 B2 | 5/2010 | Mclean et al. |
| 7,780,860 B2 | 8/2010 | Higgins et al. |
| 7,806,276 B2 | 10/2010 | Leach et al. |
| 7,832,566 B2 | 11/2010 | Leach et al. |
| 7,837,884 B2 | 11/2010 | Dorian et al. |
| 7,845,499 B2 | 12/2010 | Higgins et al. |
| 7,901,584 B2 | 3/2011 | Dorian et al. |
| 7,914,689 B2 | 3/2011 | Higgins et al. |
| 7,954,646 B2 | 6/2011 | Leach et al. |
| 7,987,995 B2 | 8/2011 | Dorian et al. |
| 7,992,725 B2 | 8/2011 | Leach et al. |
| 8,048,321 B2 | 11/2011 | Leach et al. |
| 8,062,534 B2 | 11/2011 | Higgins et al. |
| 8,067,534 B2 | 11/2011 | Jagota et al. |
| 8,119,013 B2 | 2/2012 | Leach et al. |
| 8,163,184 B2 | 4/2012 | Leach et al. |
| 8,187,477 B2 | 5/2012 | Dorian et al. |
| 8,313,954 B2 | 11/2012 | Leach et al. |
| 8,328,024 B2 | 12/2012 | Leach et al. |
| 8,337,711 B2 | 12/2012 | Dorian et al. |
| 8,474,630 B2 | 7/2013 | Dorian et al. |
| 8,567,609 B2 | 10/2013 | Landrigan et al. |
| 8,596,470 B2 | 12/2013 | Leach et al. |
| 8,603,346 B2 | 12/2013 | Leach et al. |
| 8,783,470 B2 | 7/2014 | Hecker et al. |
| 8,801,586 B2 | 8/2014 | Dorian et al. |
| 8,808,551 B2 | 8/2014 | Leach et al. |
| 8,950,586 B2 | 2/2015 | Dorian et al. |
| 8,992,862 B2 | 3/2015 | Leach et al. |
| 9,011,800 B2 | 4/2015 | Leach et al. |
| 9,114,334 B2 | 8/2015 | Leach |
| 9,239,276 B2 | 1/2016 | Landrigan et al. |
| 9,897,589 B2 | 2/2018 | Woodell-May |
| 2001/0009757 A1 | 7/2001 | Bischof et al. |
| 2002/0032112 A1 | 3/2002 | Pages |
| 2002/0035820 A1 | 3/2002 | Farris |
| 2002/0076400 A1 | 6/2002 | Katz et al. |
| 2002/0082220 A1 | 6/2002 | Hoemann et al. |
| 2002/0090711 A1 | 7/2002 | Karlsson |
| 2002/0104808 A1 | 8/2002 | Blasetti et al. |
| 2002/0114775 A1 | 8/2002 | Pathak |
| 2002/0161449 A1 | 10/2002 | Muschler |
| 2002/0169408 A1 | 11/2002 | Beretta et al. |
| 2002/0172666 A1 | 11/2002 | Sacchi et al. |
| 2002/0182664 A1 | 12/2002 | Dolecek et al. |
| 2002/0192632 A1 | 12/2002 | Hei et al. |
| 2003/0033021 A1 | 2/2003 | Plouhar et al. |
| 2003/0033022 A1 | 2/2003 | Plouhar et al. |
| 2003/0050709 A1 | 3/2003 | Noth et al. |
| 2003/0050710 A1 | 3/2003 | Petersen et al. |
| 2003/0082152 A1 | 5/2003 | Hedrick et al. |
| 2003/0118563 A1 | 6/2003 | Loeb |
| 2003/0185803 A1 | 10/2003 | Kadiyala et al. |
| 2003/0191429 A1 | 10/2003 | Andrew et al. |
| 2003/0194397 A1 | 10/2003 | Mishra |
| 2003/0205538 A1 | 11/2003 | Dorian et al. |
| 2004/0005246 A1 | 1/2004 | Efthimiadis et al. |
| 2004/0013575 A1 | 1/2004 | Stevens et al. |
| 2004/0120942 A1 | 6/2004 | McGinnis et al. |
| 2004/0171146 A1 | 9/2004 | Katz et al. |
| 2004/0182395 A1 | 9/2004 | Brookman |
| 2004/0182788 A1 | 9/2004 | Dorian et al. |
| 2004/0182795 A1 | 9/2004 | Dorian et al. |
| 2004/0251217 A1 | 12/2004 | Leach et al. |
| 2005/0076396 A1 | 4/2005 | Katz et al. |
| 2005/0084961 A1 | 4/2005 | Hedrick et al. |
| 2005/0084962 A1 | 4/2005 | Simon |
| 2005/0100536 A1 | 5/2005 | Mishra |
| 2005/0109716 A1 | 5/2005 | Leach et al. |
| 2005/0130301 A1 | 6/2005 | McKay et al. |
| 2005/0145187 A1 | 7/2005 | Gray |
| 2005/0153441 A1 | 7/2005 | Hedrick et al. |
| 2005/0153442 A1 | 7/2005 | Katz et al. |
| 2005/0186120 A1 | 8/2005 | Dorian et al. |
| 2005/0186193 A1 | 8/2005 | Mishra |
| 2005/0196393 A1 | 9/2005 | Shanbrom |
| 2005/0196874 A1 | 9/2005 | Dorian et al. |
| 2005/0247715 A1 | 11/2005 | Ellsworth et al. |
| 2005/0260174 A1 | 11/2005 | Fraser et al. |
| 2005/0260175 A1 | 11/2005 | Hedrick et al. |
| 2005/0282275 A1 | 12/2005 | Katz et al. |
| 2006/0029578 A1 | 2/2006 | Hoemann et al. |
| 2006/0051865 A1 | 3/2006 | Higgins et al. |
| 2006/0057693 A1 | 3/2006 | Simon |
| 2006/0083720 A1 | 4/2006 | Fraser et al. |
| 2006/0140923 A1 | 6/2006 | Evangelista et al. |
| 2006/0151384 A1 | 7/2006 | Ellsworth et al. |
| 2006/0175242 A1 | 8/2006 | Dorian et al. |
| 2006/0175244 A1 | 8/2006 | Dorian et al. |
| 2006/0178610 A1 | 8/2006 | Nowakowski |
| 2006/0196885 A1 | 9/2006 | Leach et al. |
| 2006/0243676 A1 | 11/2006 | Swift et al. |
| 2006/0273049 A1 | 12/2006 | Leach et al. |
| 2006/0273050 A1 | 12/2006 | Higgins et al. |
| 2006/0278588 A1 | 12/2006 | Woodell-May |
| 2007/0034579 A1 | 2/2007 | Dorian et al. |
| 2007/0036768 A1 | 2/2007 | Fraser et al. |
| 2007/0075016 A1 | 4/2007 | Leach |
| 2007/0207161 A1 | 9/2007 | Ralph |
| 2007/0208321 A1 | 9/2007 | Leach et al. |
| 2008/0011684 A1 | 1/2008 | Dorian et al. |
| 2008/0064626 A1 | 3/2008 | Zanella |
| 2008/0164204 A1 | 7/2008 | Hatamian et al. |
| 2008/0173593 A1 | 7/2008 | Coull et al. |
| 2008/0193424 A1 | 8/2008 | McKale et al. |
| 2008/0210645 A1 | 9/2008 | Coull et al. |
| 2008/0217263 A1 | 9/2008 | Higgins et al. |
| 2008/0217264 A1 | 9/2008 | Leach et al. |
| 2008/0217265 A1 | 9/2008 | Leach et al. |
| 2008/0258064 A1 | 10/2008 | Cima |
| 2008/0268064 A1 | 10/2008 | Woodell-May |
| 2008/0269762 A1 | 10/2008 | Simon et al. |
| 2008/0283474 A1 | 11/2008 | Leach et al. |
| 2008/0306431 A1 | 12/2008 | Yoo |
| 2008/0318317 A1 | 12/2008 | Roche et al. |
| 2009/0014391 A1 | 1/2009 | Leach et al. |
| 2009/0018313 A1 | 1/2009 | Shanbrom |
| 2009/0047242 A1 | 2/2009 | Reinecke et al. |
| 2009/0101599 A1 | 4/2009 | Dorian et al. |
| 2009/0112146 A1 | 4/2009 | Wratten et al. |
| 2009/0131827 A1 | 5/2009 | Crocker et al. |
| 2009/0181019 A1 | 7/2009 | Solinger |
| 2009/0192528 A1 | 7/2009 | Higgins et al. |
| 2009/0220482 A1 | 9/2009 | Higgins et al. |
| 2009/0221075 A1 | 9/2009 | Dorian et al. |
| 2009/0236297 A1 | 9/2009 | Dorian et al. |
| 2009/0250413 A1 | 10/2009 | Hoeppner |
| 2009/0253566 A1 | 10/2009 | Chavarria |
| 2009/0289014 A1 | 11/2009 | Hoeppner |
| 2009/0317439 A1 | 12/2009 | Turzi et al. |
| 2010/0007882 A1 | 1/2010 | Tang et al. |
| 2010/0015129 A1 | 1/2010 | Abramson et al. |
| 2010/0055087 A1 | 3/2010 | Higgins et al. |
| 2010/0125236 A1 | 5/2010 | Bare et al. |
| 2010/0140182 A1 | 6/2010 | Chapman et al. |
| 2010/0186676 A1 | 7/2010 | Van Der Berg |
| 2010/0189172 A1 | 7/2010 | Pateux et al. |
| 2010/0206798 A1 | 8/2010 | Dorian et al. |
| 2010/0256595 A1 | 10/2010 | Leach et al. |
| 2010/0323870 A1 | 12/2010 | Leach et al. |
| 2010/0324450 A1 | 12/2010 | Leach et al. |
| 2011/0014705 A1 | 1/2011 | Leach et al. |
| 2011/0020196 A1 | 1/2011 | Grippi et al. |
| 2011/0021334 A1 | 1/2011 | Leach et al. |
| 2011/0036786 A1 | 2/2011 | Ellsworth |
| 2011/0052561 A1 | 3/2011 | Hoeppner |
| 2011/0056893 A1 | 3/2011 | Leach et al. |

(56) References Cited

U.S. PATENT DOCUMENTS

| | | |
|---|---|---|
| 2011/0059082 A1 | 3/2011 | Germer et al. |
| 2011/0059083 A1 | 3/2011 | Aigner et al. |
| 2011/0059084 A1 | 3/2011 | Osterroth et al. |
| 2011/0065183 A1 | 3/2011 | Dorian et al. |
| 2011/0077596 A1 | 3/2011 | Higgins et al. |
| 2011/0168193 A1 | 7/2011 | Leach et al. |
| 2011/0192804 A1 | 8/2011 | Landrigan et al. |
| 2011/0251041 A1 | 10/2011 | Chavarria et al. |
| 2011/0268708 A1 | 11/2011 | Lin et al. |
| 2012/0015796 A1 | 1/2012 | Leach et al. |
| 2012/0027746 A1 | 2/2012 | Dorian et al. |
| 2012/0093936 A1 | 4/2012 | Lindenberg et al. |
| 2013/0226149 A1 | 8/2013 | Woodell-May |
| 2014/0051061 A1 | 2/2014 | Landrigan et al. |
| 2014/0054246 A1 | 2/2014 | Landrigan et al. |
| 2014/0091048 A1 | 4/2014 | Leach et al. |
| 2014/0097135 A1 | 4/2014 | Leach et al. |
| 2014/0275497 A1 | 9/2014 | Leach et al. |
| 2014/0349388 A1 | 11/2014 | Dorian et al. |
| 2015/0023939 A1 | 1/2015 | Woodell-May |
| 2018/0196030 A1 | 7/2018 | Woodell-may |

FOREIGN PATENT DOCUMENTS

| | | |
|---|---|---|
| CA | 1321138 | 8/1993 |
| CA | 2182862 | 6/1996 |
| CA | 2448415 A1 | 12/2002 |
| CN | 1074709 | 7/1993 |
| CN | 1321103 A | 11/2001 |
| CN | 1322146 A | 11/2001 |
| CN | 103702729 A | 4/2014 |
| DE | 56103 | 10/1860 |
| DE | 1443359 | 11/1968 |
| DE | 4202667 | 5/1993 |
| EP | 090997 | 10/1983 |
| EP | 0102773 | 3/1984 |
| EP | 0109374 | 5/1984 |
| EP | 0142339 | 5/1985 |
| EP | 0244834 A2 | 11/1987 |
| EP | 0253198 | 1/1988 |
| EP | 0295771 | 12/1988 |
| EP | 0417818 | 3/1991 |
| EP | 534178 | 3/1993 |
| EP | 0534178 | 3/1993 |
| EP | 0592242 | 4/1994 |
| EP | 1005910 | 6/2000 |
| EP | 1006360 A2 | 6/2000 |
| EP | 1289618 | 3/2003 |
| EP | 1406492 B1 | 4/2004 |
| EP | 1427279 A1 | 6/2004 |
| EP | 1467746 A2 | 10/2004 |
| EP | 1509326 | 3/2005 |
| EP | 1670315 A2 | 6/2006 |
| EP | 1716901 | 11/2006 |
| EP | 2558143 A1 | 2/2013 |
| EP | 2558143 A1 | 2/2013 |
| EP | 2699328 A2 | 2/2014 |
| GB | 854715 | 11/1960 |
| JP | 60-053845 | 3/1985 |
| JP | 60250014 A | 12/1985 |
| JP | 2036872 | 2/1990 |
| JP | 02071747 | 3/1990 |
| JP | 2000-189407 A | 7/2000 |
| JP | 2000199760 A | 7/2000 |
| JP | 02129224 | 10/2000 |
| JP | 2004-305439 A | 11/2004 |
| JP | 2005013783 A | 1/2005 |
| JP | 200598704 | 4/2005 |
| JP | 2005098704 | 4/2005 |
| JP | 2005524451 | 8/2005 |
| JP | 2006-305365 A | 11/2006 |
| JP | 2006527025 A | 11/2006 |
| JP | 2008104789 A | 5/2008 |
| JP | 2009-155234 A | 7/2009 |
| WO | WO-8400905 | 3/1984 |
| WO | WO-8802259 | 4/1988 |
| WO | WO-9010031 | 9/1990 |
| WO | WO-9222312 | 12/1992 |
| WO | WO-9305067 | 3/1993 |
| WO | WO-9308904 | 5/1993 |
| WO | WO-9407548 | 4/1994 |
| WO | WO-9617871 | 6/1996 |
| WO | WO-1996017871 A1 | 6/1996 |
| WO | WO-9848938 A1 | 11/1998 |
| WO | WO-0061256 | 10/2000 |
| WO | WO-0074713 A1 | 12/2000 |
| WO | WO-0103756 | 1/2001 |
| WO | WO-0183068 | 11/2001 |
| WO | WO-0238610 A1 | 5/2002 |
| WO | WO-02060925 A1 | 8/2002 |
| WO | WO-02098566 A2 | 12/2002 |
| WO | WO-03015800 | 2/2003 |
| WO | WO-03024215 A1 | 3/2003 |
| WO | WO-03/053362 A2 | 7/2003 |
| WO | WO-03/088905 | 10/2003 |
| WO | WO-03/092894 | 11/2003 |
| WO | WO-03/099412 A1 | 12/2003 |
| WO | WO-2003099412 A1 | 12/2003 |
| WO | WO-04009207 | 1/2004 |
| WO | WO-2004104553 | 12/2004 |
| WO | WO-2005/034843 A2 | 4/2005 |
| WO | WO-2006041406 A1 | 4/2006 |
| WO | WO-2007127834 A2 | 11/2007 |
| WO | WO-2007142908 A1 | 12/2007 |
| WO | WO-2007142908 A1 | 12/2007 |
| WO | WO-2008100442 A1 | 8/2008 |
| WO | WO-2008127639 A1 | 10/2008 |
| WO | WO-2009021257 A1 | 2/2009 |
| WO | WO-2009111338 A1 | 9/2009 |
| WO | WO-2011008836 A1 | 1/2011 |
| WO | WO-2011031553 A2 | 3/2011 |
| WO | WO-2011130173 A1 | 10/2011 |
| WO | WO-2012030593 A2 | 3/2012 |
| WO | WO-2012145414 A2 | 10/2012 |
| WO | WO-2012145414 A3 | 10/2012 |
| WO | WO-2012145414 A9 | 10/2012 |

OTHER PUBLICATIONS

International Search Report and Written Opinion dated Dec. 5, 2013 for PCT/US2013/056793 claiming benefit of U.S. Appl. No. 13/595,461, filed Aug. 27, 2012.

Preliminary Notice of Reasons for Rejection for Japanese Patent Application No. 2014-024420 dated Feb. 24, 2015.

Japanese Office Action dated Sep. 9, 2014 for Japan Patent Application No. 2012-520742, which claims benefit of PCT/US2010/041942 filed Jul. 14, 2010, which claims benefit of U.S. Appl. No. 12/504,413, filed Jul. 16, 2009.

"Caps for Corning® and Costar® Plastic Labware," Technical Bulletin. (Dec. 2008) Corning, Incorporated.

"Cell Isolation Techniques, Methods and Materials, Working with Enzymes," (2004) (9 pages) Worthington Biochemical Corp.

"Cell Isolation Theory, Tissue Types," (2004) (5 pages) Worthington Biochemical Corp.

"Centrifuge Tubes" CORNING Costar brochure. 1996/1997 Catalog pp. 76-77.

"Clotalyst® Autologous Clotting Factor" brochure. (Aug. 15, 2008) Biomet Biologics.

"Clotalyst® Autologous Clotting Factor. Would you like to have an autologous thrombin for rapid clotting and haemostasis?" Brochure. Biomet Biologics (Aug. 15, 2008).

"Corning® 15 and 50 mL Centrifuge Tubes," Life Sciences. (Jun. 2005) Corning Incorporated.

"Cytori Celution Cell Concentrate Device," Exhibit 14, 510(k) Summary, FDA approval K060482 (Sep. 28, 2006).

"Frequently Asked Questions, 1. Kits, 2. Enzymes," (2003) 3 pages Worthington Biochemical Corp.

"Letter CryoSeal FS System. Vaccines, Blood & Biologics," letter. (Jul. 26, 2007) FDA U.S. Food and Drug Administation. http://www.fda.gov/BiologicsBloodVaccines/BloodBloodProducts/ApprovedProducts/PremarketApprovalsPMAs/ucm091631.htm (Web accessed Aug. 12, 2011).

(56) References Cited

OTHER PUBLICATIONS

"MarrowStim™ Concentration Kit Peripheral Arterial Disease (PAD) Study" brochure. Web. Jul. 2, 2009 http://www.biomet.com/patients/clinical_recruitment_padstudy.cfm.

"MarrowStim™ Concentration System," brochure. Biomet Biologics Jun. 15, 2008.

"Plasmax® Plasma Concentration System" brochure. (Jun. 15, 2008) Biomet® Biologics.

"Prosys PRP Kit," brochure Tozai Holdings, Inc. http://tozaiholdings.en.ec21.com/Prosys_PRP_Kit--5467051_5467061.html Printed from Web Aug. 24, 2011.

"Prosys PRP Kit," Tozai Holdings, Inc. EC21 Global B2B Marketplace http://www.ec21.com/product-details/Prosys-PRP-Kit--5467061.html Printed from Web Jul. 18, 2011.

"ThermoGenesis Corp. to Supply Autologous Thrombin Kits to Biomet, Inc.," PR Newslink: http:/tinyurl.com/4h3up. (Apr. 5, 2005) http://www.noblood.org/press-releases/2128-thermogenesis-corp-supply-autologous-thrombin-kits-biomet-inc [web accessed Sep. 27, 2011].

"Trypsinization of Adherent Cells," (undated) 2 pages.

"Trypsinizing cells." Bart's Cookbook, Web. Apr. 14, 2010. http://pingu.salk.edu/~sefton/Hyper_protocols/trypsin.html.

Anesthesiology, vol. 81, No. 4, pp. 1074-1077, Oct. 1994, Hiromasa Mitsuhata, M.D., et al., "An Anaphylactic Reaction to Topical Fibrin Glue".

Ann Thorac Surg, vol. 53, pp. 530-531, 1992, Mehmet C. Oz, M.D., et al., "Autologous Fibrin Glue From Intraoperatively Collected Platelet-Rich Plasma".

Ann Thorac Surg, vol. 56, pp. 387-389, 1993, Robert L. Quigley, M.D., et al., "Intraoperative Procurement of Autologous Fibrin Glue".

Badiavas, et al., "Treatment of Chronic Wounds With Bone Marrow-Derived Cells," (Reprinted) Arch Dermatol. 139:510-516 (Apr. 2003).

Bang, N.U., et al., "Plasma Protein Requirements for Human Platelet Aggregation" Ann. N.Y. Acad Sci, 201:280-299 (1972).

Berguer, R., R. L. Staerkel, E. E. Moore, F. A. Moore, W. B. Galloway, and M. B. Mockus. "Warning: fatal reaction to the use of fibrin glue in deep hepatic wounds. Case reports." *J Trauma* 31:3 (1991): 408-11.

Berruyer, M., J. Amiral, P. Ffrench, J. Belleville, O. Bastien, J. Clerc, A. Kassir, S. Estanove, and M. Dechavanne. "Immunization by bovine thrombin used with fibrin glue during cardiovascular operations. Development of thrombin and factor V inhibitors," *J Thorac Cardiovasc Surg* 105: 5 (1993): 892-7.

BioCUE™ Platelet Concentration System, Jun. 2010. (2 pages).

Biopolymers, vol. 27, pp. 763-774, 1988, Gerald Marx, "Mechanism of Fibrin Coagulation Based on Selective, Cation-Driven, Protofibral Association".

Boomgaard, et al., "Pooled Platelet Concentrates Prepared by the Platelet-Rich-Plasma Method and Filtered with Three Different Filters and Stored for 8 Days." Vox Sanq, vol. 68: 82-89, Feb. 1995.

Brodke, et al., "Bone Grafts Prepared with Selective Cell Retention Technology Heal Canine Segmental Defects as Effectively as Autograft", SCR-Enriched Bone Grafts Heal Canine Segmental Defects, Journal of Orthopaedic Research (May 2006) pp. 857-866.

Casali, B., F. Rodeghiero, A. Tosetto, B. Palmieri, R. Immovilli, C. Ghedini, and P. Rivasi. "Fibrin glue from single-donation autologous plasmapheresis." Transfusion 32:7 (1992): 641-3.

Chinese Office Action dated Jun. 30, 2014 for Chinese Patent Application No. 201080019707.7, which claims benefit of PCT/US2010/029957 filed Apr. 5, 2010, which claims benefit of U.S. Appl. No. 12/417,789, filed Apr. 3, 2009.

Clayden J D Et Al: "Improved segmentation reproducibility in group tractography using a quantitative tract similarity measure" Neuroimage, Academic Press, Orlando, FL, US LNKD-DOI: 10.1016/J.Neuroimage. 2006.07.016, vol. 33, No. 2, Nov. 1, 2006 (Nov. 1, 2006), pp. 482-492.

Clotalyst™ Automatic Clotting Factor, Would you like to have an autologous thrombin for rapid clotting and haemostasis?, brochure, Biomet Biologics, Inc., Feb. 2007 (12 pages).

Collier, B.S. et al., "The pH Dependence of Quantitative Ristocetin-induced Platelet Aggregation: Theoretical and Practical Implications—A New Device for Maintenance of Platelet-Rich Plasma pH", Hematology Service, Clinical Pathology Department, Clinical Center, National Institutes of Health, Bethesda, Md. 20014, Blood, vol. 47, No. 5 (May 1976).

Connolly, "Injectable Bone Marrow Preparations to Stimulate Osteogenic Repair," Clinical Orthopaedics and Related Research 313:8-18 (Apr. 1995).

Connolly, John, M.D., et al. "Development of an Osteogenic Bone-Marrow Preparation." The Journal of Bone and Joint Surgery, Incorporated. vol. 71-A, No. 5 (Jun. 1989) pp. 684-691.

Dallari, et al., "In Vivo Study on the Healing of Bone Defects Treated with Bone Marrow Stromal Cells, Platelet-Rich Plasma, and Freeze-Dried Bone Allografts, Alone and in Combination," Healing of Bone Defects, Journal of Orthopaedic Research (May 2006) pp. 877-888.

De Ugarte, et al., "Comparison of Multi-Lineage Cells from Human Adipose Tissue and Bone Marrow," Cells Tissues Organs 174:101-109 (2003).

De Ugarte, et al., "Differential Expression of Stem Cell Mobilization-Associated Molecules on Multi-Lineage Cells from Adipose Tissue and Bone Marrow," Immunology Letters 89:267-270 (2003).

De Wit, et al. "Experiments on the Preparation of Blood Components with the IBM 2991 Blood Cell Processor" Vox Sang. 29: 352-362 (Feb. 10, 1975).

DelRossi, A. J., A. C. Cernaianu, R. A.Vertrees, C. J. Wacker, S. J. Fuller, J. Cilley Jr., and W. A. Baldino. "Platelet-rich plasma reduces postoperative blood loss after cardiopulmonary bypass." *J Thorac Cardiovasc Surg* 100:2 (Aug. 1990): 281-6.

DePalma, L., et al., "The preparation of fibrinogen concentrate for use as fibrin glue by four different methods." Transfusion (1993) vol. 33, No. 9; pp. 717-720.

DeUgarte, M.D., Daniel A., et al., "Future of Fat as Raw Material for Tissue Regeneration," (Feb. 2003) pp. 215-219, Lippincott Williams & Wilkins, Inc.

DiMuzio, Paul et al., "Development of a Tissue-Engineered Bypass Graft Seeded with Stem Cells," Vasucular, vol. 14, No. 6, (2006) pp. 338-342, BC Decker, Inc.

Drug Intelligence and Clinical Pharmacy, vol. 22, pp. 946-952, Dec. 1988, Dennis F. Thompson, et al., "Fibrin Glue: A Review of Its Preparation, Efficacy, and Adverse Effects as a Topical Hemostat".

Edlich, Richard F., George T. Rodeheaver, and John G. Thacker. "Surgical Devices in Wound Healing Management." In *Wound Healing: Biochemical & Clinical Aspects*,ed. I. Kelman Cohen, Robert F. Diegelmann, and William J. Lindblad. 581-600. 1st ed., vol. Philadelphia: W.B. Saunders Company, 1992.

Ehricke H H Et Al: "Visualizing MR diffusion tensor fields by dynamic fiber tracking and uncertainty mapping" Computers and Graphics, Elsevvier, GB LNKD-DOI: 10.1016/J.CAG.2006.01.031, vol. 30, No. 2, Apr. 1, 2006 (Apr. 1, 2006), pp. 255-264.

Eppley, et al., "Platelet Quantification and Growth Factor Analysis from Platelet-Rich Plasma: Implications for Wound Healing," Plastic and Reconstructive Surgery, 114(6):1502-1508 (Nov. 2004).

Epstein, G. H., R. A. Weisman, S. Zwillenberg, and A. D. Schreiber. "A new autologous fibrinogen-based adhesive for otologic surgery." *Ann Otol Rhinol Laryngol* 95 (May 25-26, 1985) 40-5.

European Communication Pursuant to Article 94(3) EPC dated May 6, 2013 for PCT/US2010/029957 which claims benefit of U.S. Appl. No. 12/417,789, filed Apr. 3, 2009.

Fibrostik™ Plasma Concentrator, Attention Operating Surgeon, Cell Factor Technologies, Inc., Jul. 2003.

First clinical results: Kuderma, H. and Helene Matras. "Die klinische Anwendung der Klebung van Nervenanastomosen mit Gerinnungssubstanzen bei der Rekonstruction verletzter peripherer Nerven." Wein Klin Wochenschr 87 (Aug. 15, 1975): 495-501.

Floryan, K. et al. "Home Study Program: Intraoperative Use of Autologous Platelet-Rich and Platelet-Poor Plasma for Orthopedic Surgery Patients" vol. 80, No. 4 (Oct. 2004) p. 667-674.

(56) References Cited

OTHER PUBLICATIONS

Frasier, John K., et al., "Plasticity of human adipose stem cells toward endothelial cells and cardiomyocytes," Nature Clinical Practice Cardiovascular Medicine, vol. 3, Supplement 1 (Mar. 2006) pp. S33-S37.

Friesen, M.D., Robert, et al. "Blood Conservation During Pediatric Cardiac Surgery: Ultrafiltration of the Extracorporeal Circuit Volume After Cardiopulmonary Bypass." Anesth. ANALG 1993: 77-702-7.

Galois, et al., "Cartilage Tissue Engineering: State-of-the-Art and Future Approaches," Pathol Biol (Paris), 53(10), Dec. 2005.

Gibble, J. W. and P. M. Ness. "Fibrin glue: the perfect operative sealant?" *Transfusion* 30 (1990): 741-7.

Gimble, Jeffrey M., "Adipose-Derived Stem Cells for Regenerative Medicine," Circulation Research (May 11, 2007) pp. 1249-1260, American Heart Association, Inc.

Gomillion, Cheryl T., et al., "Stem cells and adipose tissue engineering," Biomaterials 27, Science Direct (2006) pp. 6052-6063, Elsevier.

GPS® III System, GPS® III Platelet Separation System, Leadership through Technology, brochure, Jul. 2007 (8 sheets).

GPS® System, "GPS® Platelet Concentrate System," Cell Factor Technologies, Inc., Biomet Orthopaedics, Inc., (Feb. 29, 2004) (9 pages).

GPS® System, "Shoulder Recovery with the GPS® Platelet Concentrate System, Rotator Cuff Surgical Techniques," brochure, Cell Factor Technologies, Inc., Biomet Orthopaedics, Inc., (2004) 6 pages.

GPS® System, "Shoulder Recovery with the GPS® Platelet Concentrate System, Rotator Cuff Surgical Techniques," Cell Factor Technologies, Inc., Biomet Orthopaedics, Inc., (2004) 3 pages, http://www.cellfactortech.com/global_products.cfm, printed Sep. 16, 2005.

GPS® II System, Gravitational Platelet Separation System, "Accelerating the Body's Natural Healing Process," Biomet Biologics (Jul. 15, 2006) 16 pages.

GPS® II System, Gravitational Platelet Separation System, "Accelerating the Body's Natural Healing Process," Cell Factor Technologies, Inc., Biomet Europe (2005) 16 pages, http://www.cellfactortech.com/global_products.cfm, printed Sep. 16, 2005.

GPS® II System, Gravitational Platelet Separation System, "User Manual," Cell Factor Technologies, Inc., Biomet Europe [date unknown] 13 pages, http://www.cellfactortech.com/global_products.cfm, printed Sep. 16, 2005.

Grove, et al., "Plasticity of Bone Marrow-Derived Stem Cells," Stem Cells: Concise Review, Jan. 22, 2004.

Guilak, Frank, et al., "Adipose-derived adult stem cells for cartilage tissue engineering," Biorheology 41 (2004) pp. 389-399, IOS Press.

Harris, E.L.V. Concentration of the Extract. In. Protein Purification Methods: A Practical Approach Harris, E.L.V.; Angal, S.; Editors. (1989) Publisher: (IRL Press, Oxford, UK), pp. 67-69.

Hartman, A. R., D. K. Galanakis, M. P. Honig, F. C. Seifert, and C. E. Anagnostopoulos. "Autologous whole plasma fibrin gel. Intraoperative procurement." *Arch Surg* 127 (Mar. 1992): 357-9.

Harvest SmartPrep PRP-20 Procedure Pack, "Instructions for Use" (date unknown).

Harvest Technologies brochure, SmartPrep2 (2002).

Hattori, et al., "Osteogenic Potential of Human Adipose Tissue-Derived Stromal Cells as an Alternative Stem Cell Source," Cells Tissues Organs (2004) 178:2-12 Karger.

Haynesworth, S.E. et al. "Mitogenic Stimulation of Human Mesenchymal Stem Cells by Platelet Releasate Suggests a Mechanism for Enhancement of Bone Repair by Platelet Concentrate" 48th Annual Meeting of the Orthopaedic Research Society Poster No. 0462 (2002).

Hennis, H. L., W. C. Stewart, and E. K. Jeter. "Infectious disease risks of fibrin glue [letter]." *Ophthalmic Surg* 23 (Sep. 1992): 640.

Hernigou, et al., "Percutaneous Autologous Bone-Marrow Grafting for Nonunions. Influence of the Number and Concentration of Progenitor Cells," Journal of Bone & Joint Surgery, 87-A(7):1430-1437 (Jul. 2005).

Hom, D., et al. "Promoting Healing with Recombinant Human Platelet-Derived Growth Factor-BB in a Previously Irradiated Problem Wound." The Laryngoscope, vol. 113 (pp. 1566-1671) Sep. 2003.

Hood, Andrew G., et al., "Perioperative Autologous Sequestration III: A New Physiologic Glue with Wound Healing Properties," (Jan. 1993) vol. 14 pp. 126-129.

International Preliminary Examination Report and Written Opinion dated Aug. 31, 2010 for PCT/US2009/035564 claiming benefit of U.S. Appl. No. 61/078,178, filed Jul. 3, 2008, which priority is also claimed of said provisional case by U.S. Appl. No. 12/395,085, filed Feb. 27, 2009.

International Preliminary Report on Patentability and Written Opinion dated Oct. 13, 2011 for PCT/US2010/029957 which claims benefit of U.S. Appl. No. 12/417,789, filed Apr. 3, 2009.

International Preliminary Report on Patentability and Written Opinion dated Oct. 31, 2013 for PCT/US2012/034104 claiming benefit of U.S. Appl. No. 13/089,591, filed Apr. 19, 2011.

International Preliminary Report on Patentability completed Aug. 13, 2009 for PCT/US2008/004687 claiming benefit of U.S. Appl. No. 60/911,407, filed Apr. 12, 2007.

International Preliminary Report on Patentability dated Jan. 26, 2012 for PCT/US2010/041942 claiming benefit of U.S. Appl. No. 12/504,413, filed Jul. 16, 2009.

International Search Report and Written Opinion dated Aug. 9, 2011 for PCT/US2011/031954 claiming benefit of U.S. Appl. No. 12/758,127, filed Apr. 12, 2010.

International Search Report and Written Opinion dated Jul. 2, 2008 for International Application No. PCT/US2008/004687 which claims priority to U.S. Appl. No. 60/911,407, filed Apr. 12, 2007.

International Search Report and Written Opinion dated Jul. 3, 2009 for PCT/US2009/035564 claiming benefit of U.S. Appl. No. 61/078,178, filed Jul. 3, 2008.

International Search Report and Written Opinion dated Jul. 30, 2010 for PCT/US2010/029957 which claims benefit of U.S. Appl. No. 12/417,789, filed Apr. 3, 2009.

International Search Report and Written Opinion dated Nov. 7, 2011 for PCT/US2011/045290 claiming benefit of U.S. Appl. No. 12/846,944, filed Jul. 30, 2010.

International Search Report and Written Opinion dated Oct. 8, 2010 for PCT/US2010/041942 claiming benefit of U.S. Appl. No. 12/504,413, filed Jul. 16, 2009.

International Search Report for International Application No. PCT/US/0316506 dated Oct. 13, 2003 which claims benefit of U.S. Appl. No. 60/383,013, filed May 24, 2002.

International Search Report for International Application No. PCT/US2007/012587 dated Nov. 6, 2007 which claims benefit of U.S. Appl. No. 11/441,276, filed May 25, 2006.

International Search Report for PCT/US2012/034104 dated Oct. 29, 2012, claiming benefit of U.S. Appl. No. 13/089,591, filed Apr. 18, 2012.

Invitation to Pay Additional Fees and, Where Applicable, Protest Fee dated Aug. 6, 2012 for PCT/US2012/034104 claiming benefit of U.S. Appl. No. 13/089,591, filed Apr. 19, 2011.

Ishida, et al., "Platelet-Rich Plasma With Biodegradable Gelatin Hydrogel Promotes Rabbit Meniscal Tissue Regeneration," 52nd Annual Meeting of the Orthopaedic Research Society Paper No. 1035, 1 page (2006).

Jackson, C. M. and Y. Nemerson. "Blood coagulation." *Annu Rev Biochem* 49 (1980): 765-811).

Japan Office Action dated Aug. 23, 2013 for Japan Patent Application No. 2010-503066.

Japan Office Action dated Jan. 22, 2013 for Japan Application No. 2010-503066.

Japanese Office Action dated May 20, 2014 for Japanese Application No. JP2012-503768.

Jayadev, Suprya. "Trypsinization of Adherent Cells." Aug. 8, 1991. Web. Apr. 14, 2010 http://www.duke.edu/web/ceramide/protocols/0005.html.

(56) References Cited

OTHER PUBLICATIONS

Johnstone, et al., "Autologous Mesenchymal Progenitor Cells in Articular Cartilage Repair", Clinical Orthopaedics and Related Research 367S:S156-S162 (Oct. 1999).
Jones D K et al: "Confidence mapping in diffusion ensor magnetic resonance imaging tractography using a bootstrap approach" Magnetic Resonance in Medicine Wiley USA, vol. 53 , No. 5, May 2005 (May 2005), pp. 1143-1149.
Jorgensen, et al., "Stem Cells for Repair of Cartilage and Bone: The Next Challenge in Osteoarthritis and Rheumatoid Arthritis," Annals of Rheumatic Diseases, Aug. 2000.
Journal of Oral Maxillofacial Surgery, vol. 43, pp. 605-611, Helene Matras, M.D., "Fibrin Seal: The State of the Art" (1985).
Karpatkin, S., "Heterogeneity of Human Platelets. VI., Correlation of Platelet Function with Platelet Volume", Blood, vol. 51, No. 2 (Feb. 1978).
Kjaergard, H. K,, U. S. Weis-Fogh, H. Sorensen, J. Thiis, and I. Rygg. "A simple method of preparation of autologous fibrin glue by means of ethanol." *Surg Gynecol Obstet* 175 (1992): 72-3.
Kjaergard, H. K., Fogh Us Weis, and J. J. Thiis. "Preparation of autologous fibrin glue from pericardial blood." *Ann Thorac Sur* 55 (1993): 543-4.
Kumar, Vijay et al. "Stability of Human Thrombin Produced From 11 ml of Plasma Using the Thrombin Processing Device," Journal of American Society of Extra-Corporeal Technology. JECT: Mar. 2005:37; 390-395.
Kumar, Vijay et al. "Whole Blood Thrombin: Development of a Process for Intra-Operative Production of Human Thrombin." Journal of American Society of Extra-Corporeal Technology. JECT: Apr. 2007; 39:18-23.
Kumar, Vijay et al., "Autologous Thrombin; Intraoperative Production From Whole Blood." Journal of American Society of Extra-Corporeal Technology. JECT: Apr. 2008; 40:94-98.
Laryngoscope vol. 99, pp. 974-976, Sep. 1989, Kyosti Laitakari, M.D., et al., "Autologous and Homologous Fibrinogen Sealants: Adhesive Strength".
Laryngoscope, vol. 95, pp. 1074-1076, Sep. 1985, Karl H. Siedentop, M.D., et al., "Autologous Fibrin Tissue Adhesive".
Laryngoscope, vol. 96, pp. 1062-1064, Oct. 1986, Karl H. Siedentop, M.D., et al., "Extended Experimental and Preliminary Surgical Findings with Autologous Fibrin Tissue Adhesive Made from Patient's Own Blood".
Lasher, Lisa, M.D., "My Experience with PRP," PowerPoint presentation, http://www.cellfactortech.com/global_products.cfm, printed Sep. 16, 2005.
Lendeckel, Stefan, et al., "Autologous stem cells (adipose) and fibrin glue used to treat widespread traumatic calvarial defects: case report," Journal of Cranio-Maxillofacial Surgery (2004) European Association for Cranio-Maxillofacial Surgery.
Lerner, R. and N. S. Binur. "Current status of surgical adhesives." *J Surg Res* 48 (Feb. 1990): 165-81.
Longas, Maria O., "An Improved Method for the Purification of Human Fibrinogen." J. Biochem (1980) vol. 11, pp. 559-564.
Lori N F Et Al: "Diffusion tensor fiber tracking of human brain connectivity: acquisition methods, reliability analysis and biological results" NMR in Biomedicine Wiley UK, vol. 15, No. 7-8, Nov. 2002 (Nov. 2002), pp. 493-515.
Lu, et al., "Bone Marrow Mesenchymal Stem Cells: Progress in Bone/Cartilage Defect Repair," 19(1), Jan. 2002.
Marrowstim Concentration System, Biomet Biologics, Inc., 20 pages (REV Feb. 15, 2008).
Marx, Gerard, et al., "Heat Denaturation of Fibrinogen to Develop a Biomedical Matrix." Journal of Biomedical Materials Research Part B: Applied Biomaterials (Apr. 2007) pp. 49-57.
Masri, Marwan A., et al. "Isolation of Human Fibrinogen of High Purity and in High Yield Using Polyethylene Glycol 1000." Thromb Haemostas (Struttgart) (1983) vol. 49 (2); pp. 116-119.
Matras, Helene, H. P. Dinges, H. Lassmann, and B. Mamoli. "Zur nahtlosen interfaszikularen Nerventransplantation im Tierexperiment." Wein Med Woschtr 122:37 (1972): 517-523.
Minivalve international: duckbill valves—du 054.001 sd, <http://www.minivalve.com/htm/DV054.htm>, Accessed Jun. 30, 2014, 1 page.
Minntech® Filtration Technologies Group, "Hemocor HPH® Hemoconcentrator," Minntech Corporation (2004); http://www.minntech.com/ftg/products/hph/index.html, printed Jul. 15, 2004 (2 pages).
Minntech® Filtration Technologies Group, "Medical Applications: Blood Filtration" Minntech Corporation (2004); http://www.minntech.com/ftg/industries/medical/blood_filter.html, printed Jul. 15, 2004 (1 page).
Minntech® Filtration Technologies Group, "Renaflo® II Hemofilter," Minntech Corporation (2004); http://www.minntech.com/ftg/products/renaflo/index.html, printed Jul. 15, 2004 (2 pages).
Molnar, Amy, "Stem Cells from Muscles Can Repair Cartilage, Study Finds Genetically Engineered Muscle-Derived Stem Cells Improved Cartilage Repair in Rats", American College of Rheumatology, (2005).
Momentive Silopren*LSR 2050, Jun. 30, 2014, 3 pages.
Moretz, W., Jr., J Shea Jr., J. R. Emmett, and J Shea. "A simple autologous fibrinogen glue for otologic surgery." *Otolaryngol Head Neck Surg* 95 (Jul. 1986): 122-4.
Nakagami, Hironori, et al., "Novel Autologous Cell Therapy in Ischemic Limb Disease Through Growth Factor Secretion by Cultured Adipose Tissue-Derived Stromal Cells," Angiogenesis by Adipose Tissue-Derived Cells, (Dec. 2005) pp. 2542-2547, American Heart Association, Inc.
Nathan, Suresh,, et al., "Cell-Based Therapy in the Repair of Osteochondral Defects: A Novel Use for Adipose Tissue," Tissue Engineering, vol. 9, No. 4 (2003) pp. 733-744 Mary Ann Liebert, Inc.
Nilsson, et al., "Bone Repair Induced by Bone Morphogenetic Protein in Ulnar Defects in Dogs," The Journal of Bone and Joint Surgery, vol. 68 B., No. 4, Aug. 1986.
Notice of Allowance dated Mar. 24, 2011 for U.S. Appl. No. 12/101,586.
Notice of Allowance dated May 27, 2010 for U.S. Appl. No. 12/101,594, filed Apr. 11, 2008.
Notice of Allowance dated Oct. 18, 2011 for U.S. Appl. No. 12/897,401.
Office Action (Final) dated Mar. 18, 2010 for U.S. Appl. No. 12/101,594, filed Apr. 1, 2008.
Office Action dated Feb. 3, 2011 for U.S. Appl. No. 12/101,586, filed Apr. 14, 2008.
Office Action dated Nov. 16, 2010 for U.S. Appl. No. 12/897,401 claiming benefit of U.S. Appl. No. 12/101,594, filed Apr. 11, 2008.
Office Action dated Oct. 16, 2009 for U.S. Appl. No. 12/101,594, filed Apr. 11, 2008.
Office Action dated Sep. 20, 2010 for U.S. Appl. No. 12/101,586, filed Apr. 14, 2008.
Orphardt, Charles E., "Denaturation of Proteins," Virtual Chembook, Elmhurst College (2003) 3 pages. http://www.elmhurst.edu/~chm/vchembook/568denaturation.html (web accessed Mar. 9, 2011).
Otolaryngologic Clinics of North America, vol. 27, No. 1, pp. 203-209, Feb. 1994, Dean M. Toriumi, M.D., et al., "Surgical Tissue Adhesives in Otolaryngology-Head and Neck Surgery".
Parchment et al., Roles for in vitro myelotoxicity tests in preclincial drug development and clinical trial planning, Toxicology Pathology, Society of Toxicological Pathologists, vol. 21, No. 2, 1993, pp. 241-250.
Parchment et al., Roles for in vitro myelotoxicity tests in preclinical drug development and clinical trial planning, Toxicology Pathology, Society of Toxicological Pathologists, vol. 21, No. 2, 1993, pp. 241-250.
Parker, Anna M., et al., Adipose-derived stem cells for the regeneration of damaged tissues, Expert Opinion, Cell- & Tissue-based Therapy, Expert Opin. Biol. Ther. (2006) pp. 567-578 Informa UK Ltd.
Planat-Bénard, V., et al., "Spontaneous Cardiomyocyte Differentiation From Adipose Tissue Stroma Cells," Adipose-Derived Cell Cardiomyocyte (Feb. 6, 2004) pp. 223-229 American Heart Association, Inc.

(56) References Cited

OTHER PUBLICATIONS

Ponticiello, Michael S., "A Rapid Technique for the Isolation and Concentration of Stem Cells from Human Bone Marrow", Cell Factor Technologies, Inc. (2006) 2 pages.
Rangappa, Sunil, M.D., "Transformation of Adult Mesenchymal Stem Cells Isolated From the Fatty Tissue Into Cardiomyocytes," Adult Stem Cells Transformed into Cardiomyoctyes, (2003) pp. 775-779 Ann Thorac Surg.
Rigotti, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Breast, PRS Journal vol. 119, No. 5, Stem Cell Therapy for Angiogenesis, (Apr. 15, 2007) pp. 1409-1422.
Rubin, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Discussion vol. 119, No. 5, Stem Cell Therapy for Angiogenesis, (Apr. 15, 2007) pp. 1423-1424.
Sanal, M. "Does fibrin glue cause foreign body reactions? [letter]." Eur J Pediatr Surg 3 (1992): 190 (1 page).
Sanal, M., H. Dogruyol, A. Gurpinar, and O. Yerci. "Does fibrin glue cause foreign body reactions?" Eu r J Pediatr Surg 2 (1992): 285-6.
Schmidt, K.G., et al., "Labelling of Human and Rabbit Platelets with Indium-Oxine Complex", 23:97-106 (1979).
Schmidt, K.G., et al., "Preparation of Platelet Suspensions from Whole Blood in Buffer", Scand. J. Hoemato, 23:88-96 (1979).
Schäffler, Andreas, et al., "Concise Review: Adipose Tissue-Derived Stromal Cells—Basic and Clinical Implications for Novel Cell-Based Therapies," Tissue-Specific Stem Cells, Stem Cells® (Apr. 10, 2007) pp. 818-827 AlphaMed Press.
Semple, Elizabeth, PhD, et al. "Quality of Thrombin Produced From the Patient's Own Plasma Using the TPD™, a New Thrombin-Processing Device." Journal of American Society of Extra-Corporeal Technology. JECT: 2005; 37:196-200.
Sierra, D. H. "Fibrin sealant adhesive systems: a review of their chemistry, material properties and clinical applications." J Biomater Appl 7 (Apr. 1993): 309-52.
Sigma-Aldrich® Alkaline Phosphatase (Procedure No. 85), drug fact sheet, (2003) pp. 1-2, Sigma-Aldrich, Inc.
Silver, Frederick H., et al., "REVIEW Preparation and use of fibrin glue in surgery." Biomaterials 16 (1995) pp. 891-903.
Solem, Jan Otto, et al., "Hemoconcentration by Ultrafiltration During Open-Heart Surgery," Scand J Thor Cardiovasc Surg 22:271-274, 1988.
Sutton, Robin G., et al. "Comparison of Three Blood-Processing Techniques During and After Cardiopulmonary Bypass." Ann Thorac Surg (1993) vol. 56; pp. 941-943.
Swift, Mathew J., et al., "Characterization of Growth Factors in Platelet Rich Plasma," 1-Cell Factor Technologies, http://www.cellfactortech.com/global_products.cfm, printed Sep. 16, 2005.
Symphony II Platelet Concentrate System/PCS brochure; "Increasing bone graft bioactivity through reproducible concentrations of natural growth factors," DePuy (Jan. 2003).
Takahashi, Kazutoshi et al., "Induction of Pluripotent Stem Cells from Adult Human Fibroblasts by Defined Factors," Cell, (Nov. 30, 2007) pp. 1-12, Elsevier Inc.
The American Journal of Surgery, vol. 168, pp. 120-122, Aug. 1994, Roy L. Tawes, Jr., M.D., et al., "Autologous Fibrin Glue: The Last Step in Operative Hemostatis".
The American Surgeon, vol. 55, pp. 166-168, Mar. 1989, William D. Spotnitz, M.D., et al., "Successful Use of Fibrin Glue During 2 Years of Surgery at a University Medical Center".
The Sports Medicine Center, "Knee Cartilage Implantation", Carticel™, "Autologous Cultured Chondrocyte Implantation", http://www.orthoassociates.com/carticel.htm (printed Apr. 6, 2006).
The Stone Clinic, "Platelet Rich Plasma (PRP)", web site printed May 2006.
Vernay Product Information Sheet, Umbrella Check Valve, Part No. V251010200, Jul. 2013, 2 pages.
Weis-Fogh, U. S. "Fibrinogen prepared from small blood samples for autologous use in a tissue adhesive system." Eur Surg Res 20 (1988): 381-9.
Weisman, MD., Robert A., "Biochemical Characterization of Autologous Fibrinogen Adhesive," Laryngoscope 97: Oct. 1987; pp. 1186-1190.
Wiseman, David M., David T. Rovee, and Oscar M. Alverez. "Wound Dressings: Design and Use." In *Wound Healing: Biochemical & Clinical Aspects*,ed. I. Kelman Cohen, Robert F. Diegelmann, and WIlliam J. Lindblad. 562-580. 1st ed., vol. Philadelphia: W. B. Saunders Company, 1992.
Woodell-May, et al., "Producing Accurate Platelet Counts for Platelet Rich Plasma: Validation of a Hematology Analyzer and Preparation Techniques for Counting," Scientific Foundation, Journal of Carniofacial Surgery 16(5):749-756 (Sep. 2005).
Written Opinion of the International Preliminary Examining Authority dated Mar. 17, 2009 for International Application No. PCT/US2008/004687 which claims priority to U.S. Appl. No. 60/911,407, filed Apr. 12, 2007.
Yoon, Eulsik, M.D., Ph.D., et al., "In Vivo Osteogenic Potential of Human Adipose-Derived Stem Cells/Poly Lactide-Co-Glycolic Acid Constructs for Bone Regneration in a Rat Critical-Sized Calvarial Defect Model," Tissue Engineering, vol. 13, No. 3 (2007) pp. 619-627 Mary Ann Liebert, Inc.
Zhang, Duan-zhen, et al., "Transplantation of autologous adipose-derived stem cells ameliorates cardiac function in rabbits with myocardial infarction," Chinese Medical Journal, vol. 120, No. 4 (2007) pp. 300-307 General Hospital of Shenyang Military Region, Shenyang, China.
Zuk, Patricia A., Ph.D., "Multilineage Cells from Human Adipose Tissue: Implications for Cell-Based Therapies," Tissue Engineering, vol. 7, No. 2, (2001) pp. 211-228 Mary Ann Liebert, Inc.
Chinese Office Action dated Nov. 21, 2014 for Chinese Patent Application No. 201280030026.X.
"Australian Application Serial No. 2012245492, Response filed Jun. 22, 2017 to First Examination Report dated Aug. 22, 2016", 34 pgs.
"Australian Application Serial No. 2012245492, Response filed Aug. 3, 2017 to Subsequent Examiners Report dated Jul. 18, 2017", 36 pgs.
"Australian Application Serial No. 2012245492, Subsequent Examiners Report dated Jul. 18, 2017", 6 pgs.
"U.S. Appl. No. 14/064,859, Advisory Action dated May 5, 2015", 3 pgs.
"U.S. Appl. No. 14/064,859, Final Office Action dated Jan. 26, 2015", 17 pgs.
"U.S. Appl. No. 14/064,859, Non Final Office Action dated Jul. 8, 2014", 12 pgs.
"U.S. Appl. No. 14/064,859, Notice of Allowance dated Sep. 3, 2015", 6 pgs.
"U.S. Appl. No. 14/064,859, Response filed Apr. 27, 2015 to Final Office Action dated Jan. 26, 2015", 28 pgs.
"U.S. Appl. No. 14/064,859, Response filed Oct. 8, 2014 to Non Final Office Action dated Jul. 8, 2014", 16 pgs.
"U.S. Appl. No. 14/100,563, 312 Amendment filed Jul. 1, 2015", 7 pgs.
"U.S. Appl. No. 14/100,563, Examiner Interview Summary dated Mar. 27, 2015", 3 pgs.
"U.S. Appl. No. 14/100,563, Examiner Interview Summary dated Sep. 29, 2014", 2 pgs.
"U.S. Appl. No. 14/100,563, Final Office Action dated Dec. 23, 2014", 18 pgs.
"U.S. Appl. No. 14/100,563, Non Final Office Action dated Jun. 23, 2014", 6 pgs.
"U.S. Appl. No. 14/100,563, Notice of Allowance dated Apr. 2, 2015", 5 pgs.
"U.S. Appl. No. 14/100,563, PTO Response to Rule 312 Communication dated Jul. 28, 2015", 2 pgs.
"U.S. Appl. No. 14/100,563, Response filed Mar. 23, 2015 to Final Office Action dated Dec. 23, 2014", 11 pgs.
"U.S. Appl. No. 14/100,563, Response filed Sep. 23, 2014 to Non Final Office Action dated Jun. 23, 2014", 12 pgs.
"U.S. Appl. No. 14/510,828, Final Office Action dated Jun. 12, 2017", 13 pgs.

(56) References Cited

OTHER PUBLICATIONS

"U.S. Appl. No. 14/510,828, Non Final Office Action dated Feb. 23, 2017", 15 pgs.
"U.S. Appl. No. 14/510,828, Preliminary Amendment filed Oct. 9, 2014", 8 pgs.
"U.S. Appl. No. 14/510,828, Response filed May 23, 2017 to Non Final Office Action dated Feb. 23, 2017", 14 pgs.
"Australian Application Serial No. 2012245492, First Examination Report dated Aug. 22, 2016", 4 pgs.
"CLOTALYST™ Automatic Clotting Factor, Would you like to have an autologous thrombin for rapid clotting and haemostasis?", Biomet XP002660090., [Online]. Retrieved from the Internet: <URL:http://www.biomet.com/biologicsjinternationaljprint/BBI0004.1 081508.pdf>, (Feb. 2007), 12 pgs.
"European Application Serial No. 07795400.6, Communication Pursuant to Article 94(3) EPC dated Feb. 4, 2013", 5 pgs.
"European Application Serial No. 07795400.6, Communication Pursuant to Article 94(3) EPC dated Jul. 21, 2011", 5 pgs.
"European Application Serial No. 07795400.6, Decision to Grant dated Nov. 26, 2015", 2 pgs.
"European Application Serial No. 07795400.6, Intention to grant dated Jul. 1, 2015", 69 pgs.
"European Application Serial No. 07795400.6, Invitation pursuant to Article 94(3) and Rule 71(1) EPC dated Apr. 30, 2015", 2 pgs.
"European Application Serial No. 07795400.6, Response filed Jan. 4, 2012 to Communication Pursuant to Article 94(3) EPC dated Jul. 21, 2011", 26 pgs.
"European Application Serial No. 07795400.6, Response filed May 6, 2015 to Invitation pursuant to Article 94(3) and Rule 71(1) EPC dated Apr. 30, 2015", 99 pgs.
"European Application Serial No. 07795400.6, Response filed Aug. 9, 2013 to Communication Pursuant to Article 94(3) EPC dated Feb. 4, 2013", 13 pgs.
"European Application Serial No. 15201165.6, Extended European Search Report dated May 18, 2016", 8 pgs.
"European Application Serial No. 15201165.6, Response filed Dec. 15, 2016 to Extended European Search Report dated May 18, 2016", 11 pgs.

"GPS® II System, Gravitational Platelet Separation System", User Manual-Cell Factor Technologies, Inc., [Online]. Retrieved from the Internet: <http://www.cellfactortech.com/global _products.cfm,>, (Sep. 16, 2005), 13 pgs.
"Shoulder Recovery with the GPS® Platelet Concentrate System, Rotator Cuff Surgical Techniques", Biomet Biologics, Inc., (2004), 6 pgs.
Cancedda, Ranieri, et al., "Bone Marrow Stromal Cells and Their Use in Regenerating Bone", (Novartis Foundation Symposium 294), (2003), 133-147.
Caplan, et al., "Mesenchymal Stem Cells: Building Blocks for Molecular Medicine in the 21st Century", (TRENDS in Molecular Medicine Review) vol. 7, No. 6, (Jun. 2001), 6 pgs.
Dallari, et al., "Enhanced Tibial Osteotomy Healing with Use of Bone Grafts Supplemented with Platelet Gel or Platelet Gel and Bone Marrow Stromal Cells", The Journal of Bone and Joint Surgery, vol. 89, (2007), 2413-2420.
Dimuzio, Paul, et al., "Development of a Tissue-Engineered Bypass Graft Seeded with Stem Cells", Vasucular, vol. 14, No. 6, (2006), 338-342.
Jayadev, Suprya, "Trypsinization of Adherent Cells", (Aug. 8, 1991), 1 pg.
Morizaki, et al., "The Effects of Platelet-Rick Plasma on Bone Marrow Stromal Cell Transplants for Tendon Healing In Vitro", (2011), 1 pg.
Swift, et al., "Efficient Harvest of a Mononuclear Cell-Rich Fraction from Aspirated Bone Marrow", ORS, (Feb. 2007), 1 pg.
Welch, et al., "Citrate-based Anticoagulant Does Not Hinder Stem Cell Visability and Concentration from Bone Marrow Aspirate", (Mar. 2008), 1 pg.
"U.S. Appl. No. 14/510,828, Notice of Allowance dated Oct. 5, 2017", 5 pgs.
"U.S. Appl. No. 14/510,828, Response Filed Sep. 8, 2017 to Final Office Action dated Jun. 12, 2017", 10 pgs.
"U.S. Appl. No. 15/866,658, Preliminary Amendment filed Mar. 30, 2018", 6 pgs.
"European Application Serial No. 12721035.9, Communication Pursuant to Article 94(3) EPC dated Mar. 5, 2018", 4 pgs.

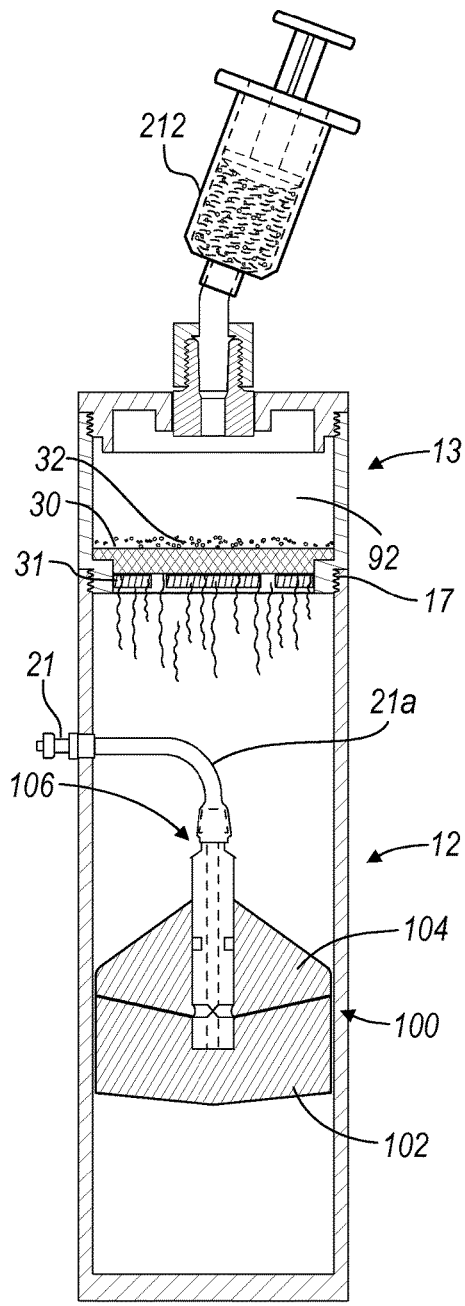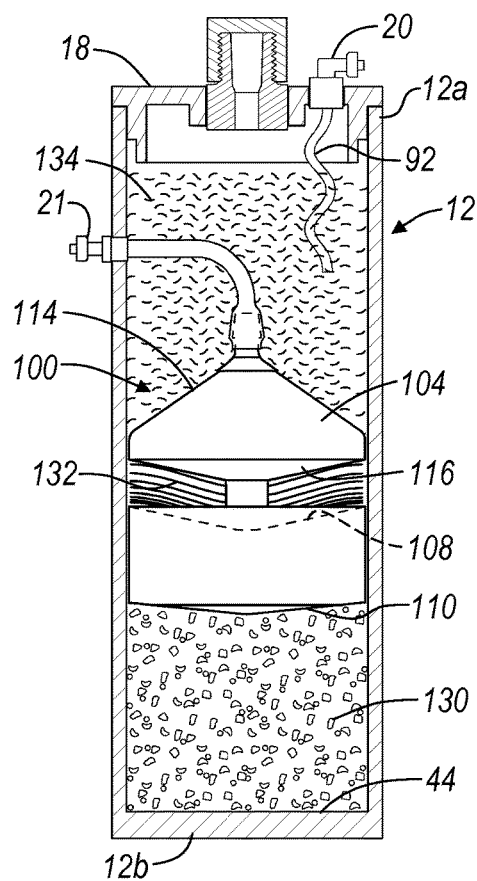
FIG. 1C
FIG. 1D

APPARATUS AND METHOD FOR SEPARATING AND CONCENTRATING FLUIDS CONTAINING MULTIPLE COMPONENTS

CROSS-REFERENCE TO RELATED APPLICATIONS

This application is a continuation of U.S. patent application Ser. No. 12/946,338; filed Nov. 15, 2010; which is a divisional of U.S. patent application Ser. No. 11/441,275, filed May 25, 2006, now U.S. Pat. No. 7,832,566, issued Nov. 16, 2010; which is a continuation-in-part of U.S. patent application Ser. No. 10/932,882, filed Sep. 2, 2004, now U.S. Pat. No. 7,374,678, issued on May 20, 2008, which is a continuation-in-part of U.S. patent application Ser. No. 10/445,381, filed May 23, 2003, now U.S. Pat. No. 7,179,391, issued on Feb. 20, 2007, which claims the benefit of U.S. Provisional Application No. 60/383,013, filed on May 24, 2002. The disclosures of the above applications are incorporated herein by reference.

FIELD

The present teachings relate to a multiple component material and an apparatus to separate and concentrate the various components. More particularly, the present teachings relate to a container operable with a centrifuge to separate and concentrate various biological components.

BACKGROUND

Multi-phase or multi-component materials where solid and fluids are combined (slurries and suspensions, for example) may be separated into the respective solid, semi-solid, or fluid components and subcomponents thereof. Complex multi-component materials may be difficult to separate because of particle sizes, fluid viscosities, interactions between the materials, etc. Depending on the desired end use of a subcomponent, separation of some multi-component materials may be too labor intensive or time consuming to warrant separating the materials.

For example, in arthroplasty procedures, the materials removed from the subject during bone bed preparation or bone reaming include a mixture of cartilage, bone chips, surrounding blood and fluids, and the dense spongy material known as bone marrow. The bone reaming materials can include beneficial undifferentiated cells, such as mesenchymal stem cells, white blood cells, and platelets which may be used to expedite the healing of the injury site and incision or may be used as therapy in other procedures. To separate the bone reaming materials into the beneficial mesenchymal stem cells is a multi-step process and can occupy hours of preparation and waiting time. An exemplary separation process includes precipitating the unwanted cells via culturing, plating, incubating the preparation, and then washing and centrifuging the preparation several times to concentrate the desired stem cells. This process is time consuming, labor intensive, and inefficient—characteristics that are neither desirable in a self-paced laboratory environment, nor desirable under surgical conditions and time restraints. Accordingly, despite the vast applications of the undifferentiated cells, white blood cells, and platelets in bone reaming material, the extensive labor in separation is too burdensome and therefore, the bone reaming material or bone reaming "debris" is discarded.

Whole blood and fluids from the arthoplasty procedure may also be discarded despite the beneficial components. Like the bone reaming material, these fluids have fractions that may be used to expedite healing and promote tissue health. For example, the whole blood may be separated into platelets, red blood cells, and plasma by density in a device such as a centrifuge. Nonetheless, these methods do not provide a simple or efficient method to extract any more than one fraction and especially a fraction other than the top fraction. Even in these systems, multiple spins may be required to effectively separate the constituents without commingling the sample. These same difficulties may be encountered even using systems incorporating a float or other device that is disposed within the sample at the interfaces of the different fractions during the centrifuge process. Additionally, the current separation systems are generally designed to separate only same phase components and do not work with multiple states of matter such as partial fluid mixtures which contain macroparticles or large sized particles, such as the bone reaming materials described above.

Therefore, it is desired to provide a device to allow for collection of selected constituents from a multi-component material having macroparticles. It is desired to provide a device to allow for the easy and reproducible removal of a particular fraction which does not happen to be the top fraction of a sample. It is desired to remove the required sample without mixing the different fractions during the extraction process. In addition, it is desired to provide a device which allows for a consistent extraction of known volumes or concentrations of the fraction elements. Moreover, it is desired to separate and concentrate a multi-state composition with one centrifugation step.

SUMMARY

An apparatus that separates and concentrates a selected fraction or component of a fluid, such as a biological fluid. For example, undifferentiated cells, such as mesenchymal stem cells, platelet fraction, buffy coat, or white blood cell fraction can be separated from bone reaming material, whole blood, bone marrow aspirate, and other materials. The apparatus, when used with a centrifuge, is generally able to create at least two fractions. It also provides for a new method of extracting the desired fraction or component or middle fraction from a sample.

The apparatus includes a container to be placed in a centrifuge after being filled with a sample. The apparatus can include a filtration system, a separation system, and an extraction system. The filtration system prevents the migration of undesired solids into the buoy system. The separation system includes a buoy or fraction separator, having a selected density that may be less than one fraction but greater than a second fraction, and is disposed in the container. In addition, a second buoy may be placed in the container with the first. The extraction system is connected to the buoy system or to the collection chamber such that the fraction in the container can be collected and drawn outside of the chamber. During the centrifuge processing, the buoy is forced away from a bottom of the container as the denser fraction collects at the bottom of the container. The buoy is generally able to physically separate the denser fraction from another fraction of the sample. The fractions can be withdrawn using the extraction system or member.

In addition to providing a first buoy and/or a second buoy, a buoy system may be provided. Generally, the buoy system may separate the sample into at least three fractions. The fractions may be separated or extracted from the container without substantially comingling the various fractions. Generally, a first buoy and a second buoy operate together to separate the sample into the various fractions and a syringe or tube may then be interconnected with a portion of the buoy system to extract the selected fractions. For example, a first buoy may be generally density tuned to a white blood cell fraction of a whole blood sample, and a second buoy tuned to a density less than the density of the undifferentiated cell fraction from bone reaming material.

According to various embodiments a method of forming at least one fraction for application relative to an anatomy is taught. The method may include obtaining a volume of a heterogeneous whole material and separating the material into the desired fraction(s). At least one of the fractions may be applied to the scaffold.

Further areas of applicability of the present teachings will become apparent from the detailed description provided hereinafter. It should be understood that the detailed description and specific examples, while indicating various embodiments of the teachings, are intended for purposes of illustration only and are not intended to limit the scope of the teachings.

BRIEF DESCRIPTION OF THE DRAWINGS

The present teachings will become more fully understood from the detailed description and the accompanying drawings, wherein:

FIG. 1C depicts a separator system being filled with a multi-component material according to various embodiments;

FIG. 1D depicts a separator system after a centrifugation process according to various embodiments;

DETAILED DESCRIPTION OF VARIOUS EMBODIMENTS

Figure 1A:
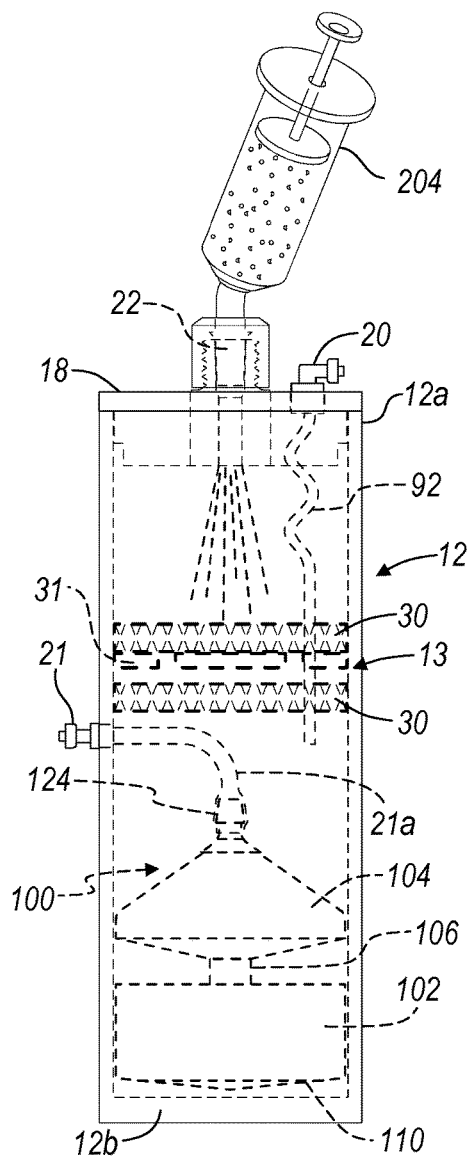
FIG. 1A is a plan view of a separator according to various embodiments.
Figure 1B:
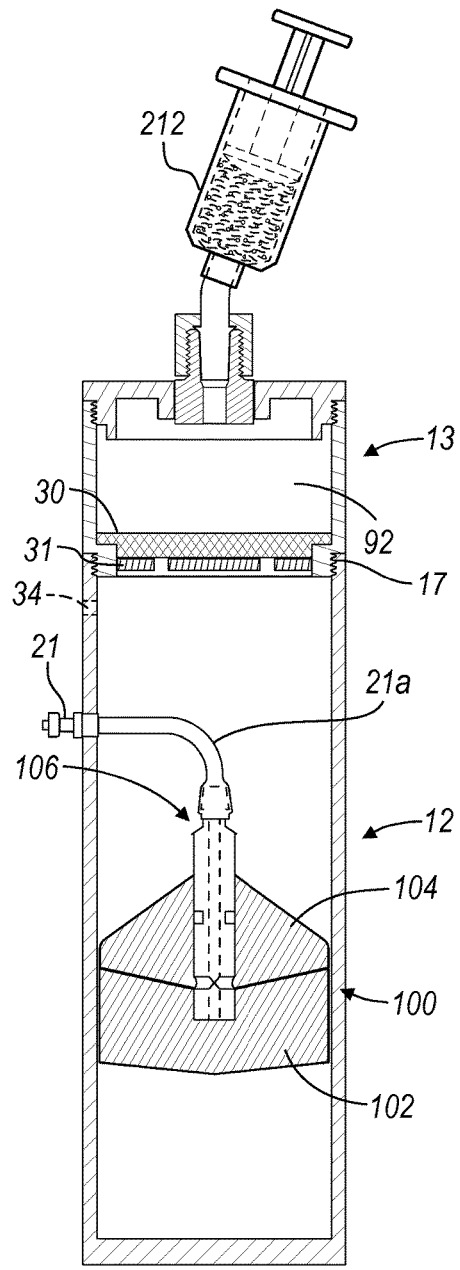
FIG. 1B depicts a separator according to various embodiments.

The following description of various embodiments is merely exemplary in nature and is in no way intended to limit the teachings, its application, or uses. Although the following description exemplary refers to bone reaming material, whole blood, and/or bone marrow aspirate separation, it will be understood that the present teachings may be used to separate and concentrate any appropriate material. It will be further understood that many multi-component materials containing macroparticles may be separated. The components or fractions are generally inter-mingled in the whole sample but may be separated with a centrifuge device that causes increased local gravity or gravitational forces.

With reference to FIGS. 1A-1D, according to various embodiments a separator 10, also referred to as a concentrator, is illustrated according to a first embodiment of the present teachings. The separator 10 generally includes a tube or container 12 that is adapted to hold a multi-component sample, such as a mixture of a bone reaming material and an anti-coagulated whole blood sample, for further processing. The tube 12 includes a top or open end 12a, which is closeable, and a bottom or closed end 12b. The bottom 12b may also be selectively closeable. Disposed within the tube 12 is a filtration system or member 13 and a separation system or buoy 14, 300. The filtration system 13 and the buoy 14, 300 are in fluid communication within the tube 12. The buoy 14, 300 is generally nearer the bottom end 12b of the tube 12 rather than the open end 12a. The buoy 14, 300 is able to move along a central axis A of the tube 12. A cap 18 substantially mates with the open end 12a of the tube 12 to close the tube 12 save for ports formed in the cap 18. Extending from the cap 18 is a plasma valve or port 20 that communicates with an area, described further herein, within the tube 12 defined between the buoy 14, 300 and the cap 18. It will be understood that the plasma port 20 is merely exemplary in nature and simply allows for removal of a selected fraction of a sample, such as plasma from the mixture of bone reaming material and whole blood.

Although the tube 12 is described here as a cylinder, it will be understood that other shapes may be used, such as polygons. The internal portions, such as the cap 18, filtration system 13, and buoy 14, 300, would also include this alternate shape. Preferably the tube 12 is formed of a thermal plastic material which is flexible under the forces required to separate multi-component biological materials such as a mixture of bone reaming material and whole blood. The tube 12 may be made of a material that includes the properties of both lipid and alcohol resistance. These properties help increase the separation speed and decrease the amount of material which may cling to the tube wall 23. For example, Cyrolite MED2® produced by Cyro Industries of Rockaway, N.J. may be used to produce the tube 12.

The tube 12 has a tube wall 23 with a thickness of between about 0.01 millimeters and about 30.0 millimeters, although the tube wall 23 may be any appropriate thickness. The thickness of the tube wall 23 allows the tube wall 23 to flex during the centrifuge process yet be rigid enough for further processing of a bone reaming debris and blood sample disposed in the tube 12. The tube 12 is closed at the bottom end 12b with a tube bottom 24 formed of the same material as the tube wall 23 and is formed integrally therewith. Generally the tube bottom 24 has a thickness which is substantially rigid under the forces required to separate the sample such that it does not flex.

The cap 18 provides a structure to substantially close the tube 12. The cap 18 particularly includes a plate 26 that has an external circumference substantially equal to the external circumference of the tube 12. Extending from the plate 26 and into the tube 12 is a flange 28. The external circumference of the flange 28 is substantially equal to the internal circumference of the tube 12. In this way, the cap 18 substantially closes the tube 12. It will be understood the cap 18 may be in any form so long as the cap 18 substantially closes and/or seals the tube 12 when installed.

The filtration system 13 is generally near the open end 12a of the tube. The filtration system 13 prevents migration of unwanted solid materials, such as macroparticles 32, through the filter and past the buoy 14, 300. The macroparticles 32 can be used for other purposes, such as void filling, but can be selected to not be further separated within the tube 12.

The filtration system 13 can comprise a mesh 30. The mesh 30 can be made of a rigid material such as high molecular weight PTFE. The mesh 30 can be rigid enough to support a mass during a centrifuge procedure. Alternatively, or in addition thereto, a support can be provided to support the mesh and the macroparicles during a selected procedure. For example, a filter plate 31 can be provided to support the mesh 30. The filter plate 31 can includes spacers large enough to allow a material to pass there through, but also support the mesh 30.

The mesh 30 can have a pore or mesh size that is of a sufficient diameter to prevent passage of unselected solid materials or macroparticles 32 through the filtration system 13. An example mesh size useful in the separation and concentration of a mixture of bone reaming material and whole blood is from about 10 micrometers to about 200 micrometers. In various embodiments, the mesh size is less than about 50 micrometers. It is understood that the mesh size may be modified depending on the fine or coarse nature of the bone reaming and the resultant sized macroparticles 32. As used herein, "macroparticle" refers to a solid or semi-solid material having a greater diameter than the pores used in the filtration system 13. For example, where the mesh 30 has a pore size of about 50 micrometers, the macroparticle 32 has a greatest cross-section length of greater than about 50 micrometers. In yet another example, where the mesh size is about 1 centimeter, the macroparticle 32 would have a cross-section length of greater than about 1 centimeter.

Figure 2A:
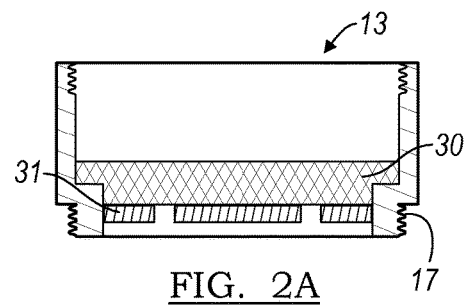
FIG. 2A depicts a filtration system according to various embodiments.
Figure 2B:
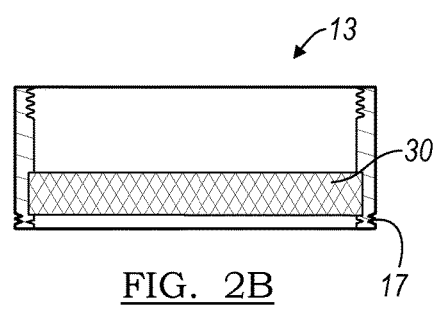
FIG. 2B depicts a filtration system according to various embodiments.

The filtration system 13 may be provided to be separable from the tube 12. For example, a seam or break 34 can be formed on the tube 12 such that the filtration system 13 and macroparticles 32 collected therein can be easily removed from the tube 12. The break 34 may include perforations or scoring that allows for removal either by hand manipulation from a user (such as snapping off the filtration system) or require the use of a tool to cut or remove the filtration member. As depicted in FIGS. 2A and 2B, filtration system 13 can also include threads 17 as a mechanism to separate the filtration system from the tube 12. The threads 17, or similar separation mechanism, can allow for re-attaching the cap 18 to the top end 12a of the tube 12 after unscrewing and removing the filtration system 13.

As illustrated in FIG. 1A, multiple mesh filters 30 can be included in the filtration system 13. Each mesh 30 filter may have a different pore size to enhance the trapping of macroparticles in the filtration system 13. For example, it may be desirable to have a mesh 30 located closest to the cap 18 having a greater mesh size than another mesh 30 located nearer the buoy 14, 300. As disclosed later herein, the filtration system 13 may be used to collect bone particles useful for filling bone voids. In various embodiments the material provided to the tube 12 can include reaming debris from bone, a blood sample, or other portions that may define a whole sample. The whole sample can be placed in the tube 12 to separated according to various embodiments.

The separation system 10 can also includes the buoy 14, 300 to assist in separation and extraction of selected fractions from the whole sample. The buoys 14, 300 can include an upper or collection face 46 that defines an inverse cone or concave surface. Generally the cone has an angle of between about 0.5° to about 45°, and may be about 0.5° to about 90° from a vertical axis, wherein the apex of the cone is within the buoy 14, 300. The collection face 46 forms a depression in the buoy 14, 300 which collects and concentrates material during the separation process. Additionally, the buoy 14, 300 has a bottom face 40 that defines an inverse cone, dome, or covered surface. The buoy bottom face 40 includes an apex 42 that engages the tube bottom 24 before a buoy edge 44 engages the tube bottom 24. The buoy 14, 300 includes a material that is a substantially rigid such that the buoy edges 44 never meet the tube bottom 24. Therefore, there is a gap or free space 46 formed between the buoy edge 44 and the tube bottom 24 along the perimeter of the buoy 14, 300.

The separator 10 is generally provided to separate a multi-component material that can have macroparticles 32 that includes various components or constituents of varying densities that are commingled or mixed together. The separator 10 includes the buoy 14, 300 that is of a selected density depending upon a selected constituent of the multi-constituent material. Although the buoy 14, 300 may be tuned or of any selected density, the following example relates to separation of a bone reaming debris and whole blood mixture into various components. Therefore, the buoy 14, 300 will be discussed to include a selected density relative to bone reaming material and whole blood separation. It will be understood, however, that the buoy 14, 300 may be of any appropriate density depending upon the multi-component fluid being separated.

The buoy 14, 300 may be formed of any appropriate material that may have a selected density. With bone reaming materials, selected materials can include white blood cells, platelets, or undifferentiated cells, including, but not limited to mesenchymal stem cells. For example, when the separator 10 is to separate blood, the buoy 14, 300 generally has a density which is greater than that of platelets, red blood cells, and white blood cells in a bone reaming material and whole blood sample, but less than the undifferentiated cell fraction of the sample. For bone reaming material and whole blood mixtures, the density of the buoy 14, 300 is generally between about 1.02 g/cc and about 1.09 g/cc. This range is sufficient to separate at least red blood cells from the other fractions. The bone reaming debris and whole blood mixture (or saline) provides a choice of several desirable fractions, such as the white blood cells, platelets, and undifferentiated cells discussed herein. The value of 1.02 g/cc to about 1.09 g/cc is given only as a benchmark, assuming that the desired collection fraction is the platelet fraction or the undifferentiated stem cells as the value segregates the white and red blood cells from the other fractions. If for example, a different fraction was desired for collection, the density fraction, or a slightly higher density, would be an appropriate for the buoy to separate the undesired fraction.

To achieve the selected density, the buoy 14, 300 may be formed as a composite or multi-piece construction, including a plurality of materials. Particularly, a first or outside portion 48 defines the collection face or surface 38 and the buoy edge 44 and is formed of the same material as the tube 12. The outside portion 48 defines a cup or void into which a plug or insert 50 is placed. The insert 50 has a mass such that the density of the entire buoy 14, 300 is within the selected range, for example the range described above. Generally, a high density polyethylene may be used, but the material and size of the insert 50 may be altered to produce the desired density of the buoy 14, 300. Alternatively, the buoy 14, 300 may be formed of a single suitable material that has a density in the selected range. Nevertheless, the buoy 14, 300 formed unitarily or of a single material would still include the other portions described in conjunction with the buoy 14, 300.

The outside portion 48 of the buoy 14, 300 also defines the outside circumference of the buoy 14, 300. The outside circumference of the buoy 14, 300 is very close to the internal circumference of the tube 12. Due to the operation of the buoy 14, 300, however, described further herein, there is a slight gap between the outside of the buoy 14, 300 and the inside of the tube 12. Generally, this gap is between about 1 and about 10 thousandths of an inch around the entire circumference of the buoy 14, 300. Generally, it is desired that the distance between the outside circumference of the buoy 14, 300 and the inside circumference of the tube 12 is great enough to allow a selected material or component to pass. For example, in bone reaming material the distance is selected so that white and red blood cells may pass through the gap without being lysed, damaged, or activated.

Figure 3A:
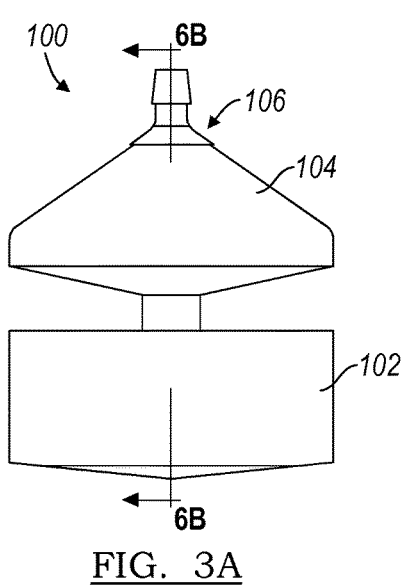
FIG. 3A is a side plan view of a buoy system according to various embodiments.
Figure 3B:
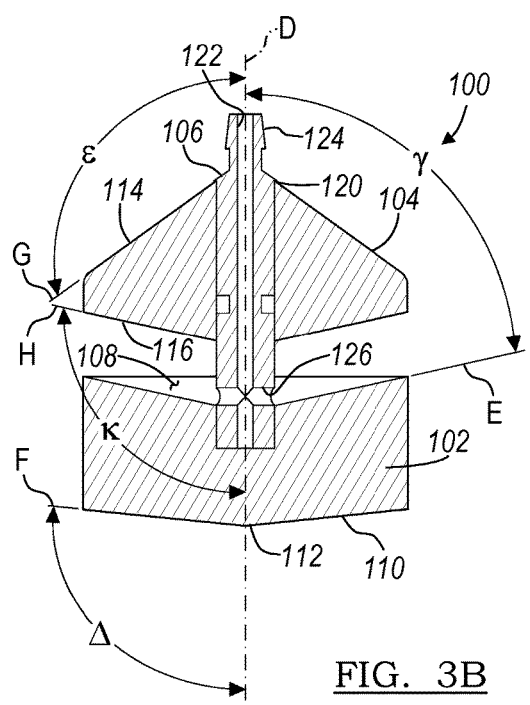
FIG. 3B is a cross-sectional view of the buoy system of FIG. 3A.

Referring to FIGS. 3A and 3B, a buoy system 100 is illustrated. The buoy system 100 generally includes a first buoy or fraction separator member 102 and a second buoy member or fraction separator 104. The first buoy 102 and the second buoy 104 may be operably interconnected with a buoy system cylinder or member 106. The buoy system 100 may be placed in a tube, such as the tube 12. The tube 12 may be formed of any appropriate material, such as the Cryolite Med® 2 as discussed above. Nevertheless, the buoy system 100 may be designed to fit in the tube 12 or may be formed to fit in any appropriate member that may be disposed within a selected centrifuging device. It will be understood that the following discussion relating to buoy system 100 to be substantially matched to the size of the tube 12 is merely exemplary. As the buoy 14, 300 may be sized to fit in any appropriate tube, the buoy system 100 may also be sized to fit in any appropriate tube. It will be further understood that the tube 12 may be any appropriate shape. The tube 12 need not only be cylindrical but may also be or include conical portions, polygonal portions, or any other appropriate shapes.

The first buoy 102 of the buoy system 100 may be generally similar in geometry to the buoy 14, 300. It will be understood that the first buoy member 102 may be formed in the appropriate manner including shape or size to achieve selected results. Nevertheless, the first buoy member 102 generally includes an exterior diameter that may be slightly smaller than the interior diameter of the tube 12. Therefore, the first buoy member 102 may be able to move within the tube 12 during the centrifugal process. Also, as discussed above, the tube 12 may flex slightly during the centrifuging process, thus allowing the first buoy member 102 to include an exterior diameter substantially equivalent to the interior diameter of the tube 12. As discussed further herein, during the centrifugation process, a portion of the fraction of a sample may pass between the exterior wall of the first buoy member 102 and the tube 12.

The first buoy member 102 may generally include a density that is substantially equivalent to a first or selected fraction of the sample. If the sample to be separated includes bone reaming material and is desired to separate the white/red blood cells from the other portions of the sample, the first buoy member 102 may have a selected density that may be about 1.00 grams per cc (g/cc) to about 1.10 g/cc. It will be understood that the density of the first buoy member 102 may be any appropriate density, depending upon the fraction to be separated, and this range of densities is merely exemplary for separating white/red blood cells from a whole blood sample.

In addition, the first buoy member 102 includes a collection face or area 108 at a proximal or upper portion of the first buoy member 102. The collection face 108 generally defines a concave area of the first buoy member 102 and may have a selected angle of concavity. The buoy assembly 100 defines a central axis D. The collection face 108 defines a surface E that is formed at an angle γ to the central axis D of the buoy system 100. The angle γ may be any appropriate angle and may be about 0.5° to about 90°. The angle γ may, however, be between about 45° and 89.5°. Nevertheless, it will be understood that the angle γ may be any appropriate angle to assist in collection of a selected fraction or portion of the sample by the first buoy member 102.

A bottom or lower surface 110 of the first buoy member 102 may define a bottom face. The bottom face 110 may also be formed at an angle D relative to the central axis D. The bottom surface 110 defines a surface or plane F that may be formed at an angle Δ relative to the central axis D of the buoy system 100. The angle Δ may be any appropriate angle and may be about 90° to about 180°. For example, the angle Δ may be about 105°. Similarly to the buoy bottom face 40, the bottom surface 110 defines an apex 112 that may first engage the bottom 12b of the tube 12, such that most or the majority of the bottom surface 110 does not engage the tube 12. As illustrated further herein, the apex 112 allows for a free space or gap to be formed between the bottom face 110 of the first buoy member 102 and the bottom 12b of the tube 12.

The second buoy member 104 may include an outer diameter substantially equivalent to the outer diameter of the first buoy member 102. Therefore, the second buoy 104 may move with the first buoy 102, particularly if the second buoy 104 is interconnected with the first buoy 102 with the buoy central cylinder 106. Nevertheless, the second buoy member 104 may be allowed to move substantially freely within the tube 12 during the centrifuging process.

The second buoy member 104 also includes an upper or superior surface 114 that defines a plane G that is formed at an angle relative to the central axis D of the buoy system 100. The angle ε of the plane G relative to the central axis D of the buoy system 100 may be any appropriate angle. For example, the angle ε may be about 90° to about 180°. Generally, the angle ε may assist in allowing a selected fraction or a portion of the sample to pass over the top surface 114 and past the second buoy member 104 during the centrifuging process.

The second buoy member 104 also define a bottom or inferior surface 116 that also defines a plane H that may be formed at an angle K relative to the central axis D of the buoy system 100. The angle K may be any appropriate angle, such as about 90° to about 150°. Nevertheless, the angle K may be convex and substantially complimentary to the angle γ of the collection face 108 that may be concave of the first buoy member 102. For example, if the angle γ is about 80°, the angle K may be about 80° as well so that the surfaces 316 and 308 mate as the first buoy member 102 engages the second buoy member 104. This may be for any appropriate reason, such as extraction of a fraction that may be disposed near the collection face 108 of the first buoy member 102. Nevertheless, the angle K may be any appropriate angle as the angle γ.

The second buoy member 104 may be formed to include any appropriate density. For example, the second buoy member 104 may include a density that is less than the plasma fraction of a bone reaming material and whole blood sample. It will be understood that the second buoy member 104 may include any appropriate density and a density that is less than the undifferentiated cell and/or platelet fractions of a bone reaming material blood sample is merely exemplary. Nevertheless, if a bone reaming material sample is desired to be separated and the plasma sample is to be substantially separated from another fraction, the second buoy member 104 may include a density that is less than the plasma fraction. Therefore, the density of the second buoy member 104 may be about 0.01 g/cc to about 1.03 g/cc.

The buoy post 106 may operably interconnect the first buoy member 102 and the second buoy member 104. The buoy post 106 may be any appropriate connection member. The buoy post need not be a single cylindrical portion. For example the buoy post 106 may include one or more members interconnecting the first buoy member 102 and the second buoy member 104, such as around a perimeter thereof. In addition, the buoy post 106 may include any appropriate shape or geometry.

The buoy system post 106 may be rigidly affixed to the first buoy member 102 and the second buoy member 104, such that the first buoy member 102 may not move relative to the second buoy member 104 and vice versa. Alternatively, the buoy post 106 may be slidably connected to either or both the first buoy member 102 and the second buoy member 104. According to various embodiments, the buoy post 106 is generally fixedly connected to the first buoy member 102 and slidably interconnected to the second buoy member 104. The buoy post 106 may include a catch portion or lip 120 that is able to engage a portion of the second buoy member 104, such that a range of travel of the second buoy member 104, relative to the first buoy member 102 is limited. Nevertheless, the range of travel of the second buoy member 104 towards the first buoy member 102 may be substantially unlimited until the second buoy member 104 engages the first buoy member 102.

The buoy post 106 may also define a central cannula or bore 122. The post bore 122 may include a connection portion 124 substantially defined near an upper or a proximal end of the buoy post 106. This may allow for interconnection of various components with the buoy post 106, such that various components may be moved through the bore 122 from an exterior location. The buoy post 106 may also define a port or cannula 126 that connects the post cannula 122 with the collection face 108. Therefore, a substance may travel through the post cannula 122 and through the port 126. Various substances may then be provided to or removed from the collection face 108 of the first buoy member 102.

The tube 12 may include the cap 18 that further defines a plasma valve or port 20. Extending through the cap 18 and interconnecting with a first flexible tube or member 54, the plasma port 20 may be used to extract plasma of the sample that is positioned above the second buoy member 104. The tube 12 may also define a second port 21, which may also be referred to as a plasma rich port (PRP). As discussed herein, a second flexible member, such as a flexible tube 21a, may interconnect the PRP port 21 and a connection portion 124 of a buoy cylinder 106.

Other portions of the separator system 10, particularly those portions of the tube 12 and the cap 18 that have various valves connected therewith may be included in the tube 12 and used with the buoy system 100. Nevertheless, once the buoy system 100 is interconnected, it may be positioned in the interior of the tube 12 and the syringe 200 used to place a sample into the tube 12.

The multi-component sample may be positioned in the separator 10 adjacent to the filtration system 13 for separation and concentration. The bone reaming material, whole blood, bone marrow aspirate, or other materials may be positioned by inserting the materials using a syringe through the port 22 or by removing the cap 18 and spreading the multi-component material into the region above the filtration system 13. In the latter placement method, the cap 18 is screwed or otherwise secured into place on the separator 10. Additional materials can be added to the multi-component sample to maintain the integrity of the sample, such as an anticoagulant. It will also be understood that various centrifuge times or forces may be altered depending upon the exact material that is being separated with the separator 10. It will also be understood that the separation of bone reaming material, a mixture of whole blood and bone reaming material, or whole blood, are merely exemplary of the materials that may be separated using the separator 10. It will be understood that two buoys 102 and 104 may generally be near one another when the sample is positioned in the tube 12, but are illustrated apart for clarity of the present discussion.

After the sample is positioned within the tube 12, as described above, a cap may be positioned over the port 22, such that the sample is not allowed to escape from the tube 12. After the sample is placed in the tube 12 and the cap 52 placed on the port 22, the tube 12 including the sample and the buoy system 100 may be centrifuged. The system 10 may remain stationary for a selected amount of time prior to centrifuging to allow the components of the bone reaming material and whole blood mixture, other than macroparticles 32, such as bone fragments, cartilage, etc. to transverse the filter and collect in the tube 12.

With reference to FIG. 1D, after a centrifugation of the tube 12, including the buoy system 100, substantially three fractions of the sample may be formed. After the bone reaming material sample is delivered to the tube 12, the separator 10 is placed in a centrifuge. The centrifugation forces affect the tube wall 23. The forces compress the tube 12 linearly along axis A thereby bowing or flexing the tube wall 23. As the tube wall 23 compresses it increases the diameter of the tube 12 making it easier for the buoy 14, 300 to move in the direction of the top 12a of the tube 12. In addition, the bottom face 48, defining an inverse cone, helps the initial movement of the buoy 14, 300. Because the buoy 14, 300 is not substantially flat along its bottom, it does not form a vacuum interaction with the tube bottom 24. Therefore, the initial movement of the buoy 14, 300 away from the tube bottom 24 is quicker than if the bottom of the buoy 14, 300 was flat.

During the centrifuge process the white/red bloods cells of the white/red blood cell fraction 222 force the buoy 14, 300 in the direction of the top 12a of the tube 12 because the buoy 14, 300 is less dense than the white/red blood cell fraction 222. Although the bone reaming material, including the white/red blood cells is loaded above the buoy 14, 300, the red blood cells are able to move between the buoy 14, 300 and the tube wall 23 because the circumference of the buoy 14, 300 is less than the internal circumference of the tube 12. During the centrifuge process the buoy 14, 300 stops at an interface of a plasma fraction 224 and the white/red blood cell fraction 222 because of the selected or tuned density of the buoy 14, 300.

With particular reference to FIG. 1D, the centrifuge process has been completed and the buoy 14, 300 has moved to the interface of the white/red blood cell fraction 222 and plasma fraction 224. After the centrifuge has slowed or stopped, and before or after the tube 12 has been removed from the centrifuge, the tube wall 23 decompresses which helps support the buoy 14, 300 at the interface position. It is also understood that applying an external pressure to the tube 12 via fingers or another apparatus may help stabilize the buoy 14, 300 during the plunging procedure described herein.

A first fraction 130 may be positioned between the bottom face 110 and the bottom of the tube 24. A second fraction may be positioned between the collection face 108 and the bottom surface 116 of the second buoy 104. In addition, a third fraction may be positioned between the upper surface 114 and the cap 18 of the tube 12. Generally, the first fraction 130, the second fraction 132, and the third fraction 134 are substantially physically separated with the buoy system 100. During the centrifugation process, the tube 12 may flex slightly to allow for ease of movement of the buoy system 100 through the tube 12 and the sample. Nevertheless, the buoy system 100, during the centrifugation process, substantially creates the three fractions 130, 132, and 134 without the operation of an operator. Therefore, the formation of at least three fractions may be substantially simultaneous and automatic using the buoy system 100.

The buoy system 100 substantially separates the fractions 130, 132, and 134, such that they may be easily removed from the tube 12. For example, with reference to FIG. 1D, a syringe or other instrument 140 may be used to extract the second fraction 132 by interconnecting a cannula or bored tube 142 with the connection portion 124 of the buoy cylinder 106. By drawing the plunger 144 into the extraction syringe 140, a vacuum or upward force is produced within the extraction syringe 140. This force draws the second fraction 132 through the ports 126 of the buoy post 106 and through the buoy cannula 122. Therefore, the second fraction 132 may be extracted from the tube 12 without substantially comingling the second fraction 132 with either the first fraction 130 or the third fraction 134. The second fraction 132 is drawn in the direction of arrow M through the cannula 122 and into the extraction syringe 140.

It will be understood that the second tube 21a may also be used. The extraction syringe 140 may be interconnected with the PRP 21 that is interconnected with the connection portion 124 of the buoy cylinder 106. As discussed herein the buoy cylinder allows access to the platelet rich area between the buoy portions. Thus, it will be understood, that access may be obtained and the platelet rich portion of the sample, between the two buoys, may be extracted in a plurality of ways. The illustrations and method described herein is merely exemplary.

Alternatively, if the post 106 is not provided other portions may be provided to gain access to the second fraction 132. For example, if a plurality of members are provided around the perimeter of the first buoy 102 and the second buoy 104 a valve portion, such as a puncture-able valve, may be provided in the second buoy 104 to be punctured with an object. In this way an extraction needle may puncture the valve to gain access to the second fraction 132. Regardless, it will be understood that the buoy system 100 may be able to form a plurality of fractions, such as the three fractions 130, 132, and 134 and at least the second fraction 132 may be extracted without substantially commingling the various fractions.

During the extraction of the second fraction 132 through the cannula 122, the second buoy member 104 may move in the direction of arrow M towards the first buoy member 102. As described above, the collection face 108 of the first buoy member may include an angle γ that is substantially complementary to the bottom face 116 of the second buoy member 104. Therefore, if the second buoy member 104 is allowed to move along the buoy cylinder 106, the bottom face 116 of the second buoy member 104 may be able to substantially mate with the collection face 108 of the first buoy member 102. Alternatively, if the second buoy member 104 is not allowed to move, the second buoy member may be provided with a vent port or valve, such that the extraction of the second fraction 132 from the collection face 108 may not be hindered by the buildup of undesirable forces. Nevertheless, if the second buoy member 104 may move, the interaction of the bottom face 116 of the second buoy member 104 may assist in substantially removing the entire second fraction 132 from the tube 12. As described above, the bottom face 84 of the plunger 16 may also serve a similar purpose when engaging the collection face 46 of the buoy 14, 300.

Once the second fraction 132 has been extracted from the tube 12, the second buoy member 104 may substantially mate with a portion of the first buoy member 102. As discussed above, the second buoy member 104 may substantially only mate with the first buoy member 102 if the second buoy member 104 is able to substantially move relative to the first buoy member 102. Therefore, it will be understood that the second buoy member 104 need not necessarily mate with the first buoy member 102 and is merely exemplary of an operation of various embodiments. Nevertheless, once the second fraction 132 has been extracted from the tube 12, the port 21 may be used in conjunction with a selected instrument, such as a plasma extraction syringe 200 to remove the plasma or the third fraction 134 from the tube 12 using the extraction tube 54 interconnected with the port 20.

As described above, the tube 54 allows for extraction of the third fraction 134 from the tube 12 without commingling the third fraction 134 with the remaining first fraction 130 in the tube 12. Therefore, similar to the separator and extraction system 10, three fractions may be substantially formed within the tube 12 with the buoy system 100 and may be extracted without substantially commingling the various fractions. Once the third fraction 134 is extracted from the tube 12, the buoy system 100 may be removed from the tube 12, such that the first fraction 130 may be removed from the tube 12. Alternatively, the first fraction 130 may be discarded with the tube 12 and the buoy system 100 as a disposable system. Alternatively, the system may be substantially reusable, such that it can be sterilized and may be sterilized for various uses.

The description of the method of use of the buoy system 100 is exemplary of a method of using a system according to various other embodiments. It will be understood, however, that various specifics may be used from various embodiments to allow for the extraction of selected fractions. For example, the centrifugation process may be substantially a single step centrifugation process. The buoy system 100, according to various embodiments, may allow for the formation of three fractions during a single centrifugation process.

The separator 10 is then spun in the centrifuge in a range between about 1,000 and about 8,000 RPMs. This produces a force between about 65 and about 4500 times greater than the force of normal gravity, as generally calculated in the art, on the separator 10 and the bone reaming material sample placed in the separator 10. At this force, the more dense material in a bone reaming material sample is forced towards the bottom 12*b* of the tube 12. The dense material, such as white and red blood cells or a white/white/red blood cell fraction 222, collects on the tube bottom 24. Because the buoy 14, 300 has a density that is less than the white/red blood cell fraction 222, it is forced in a direction toward the top 12*a* of the tube 12 in the centrifuge. Nevertheless, because the buoy 14, 300 is denser than a plasma fraction 224, the buoy 14, 300 does not reach the top 12*a* of the tube 12.

Figure 4:
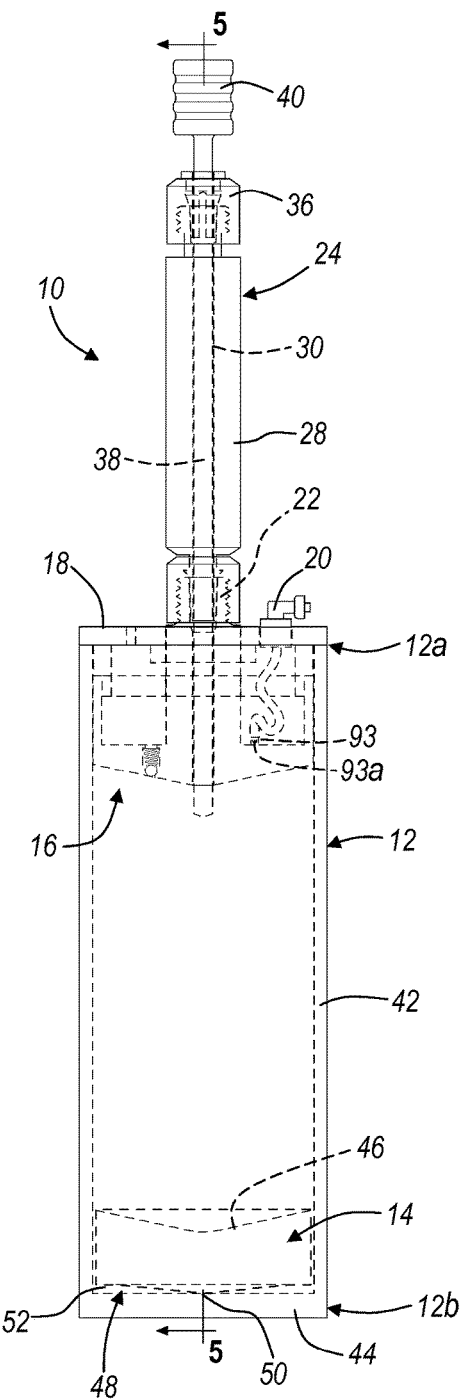
FIG. 4 is a plan view of a separator including a plunger in a tube according to a second embodiment of the present teachings.
Figure 5:
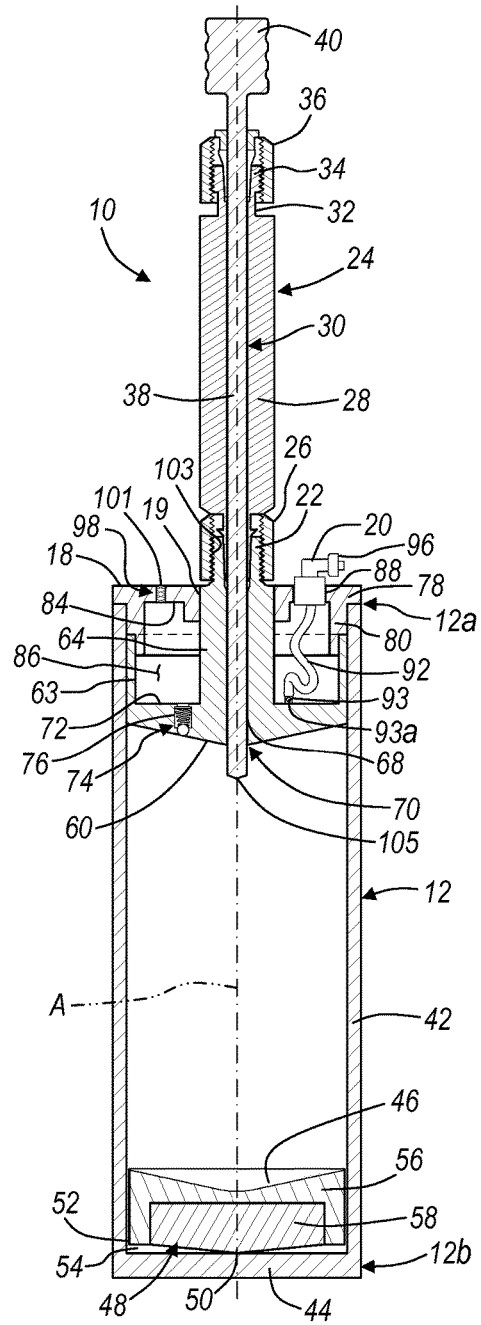
FIG. 5 is a cross-section view taken along line 5-5 of FIG. 4.
Figure 6:
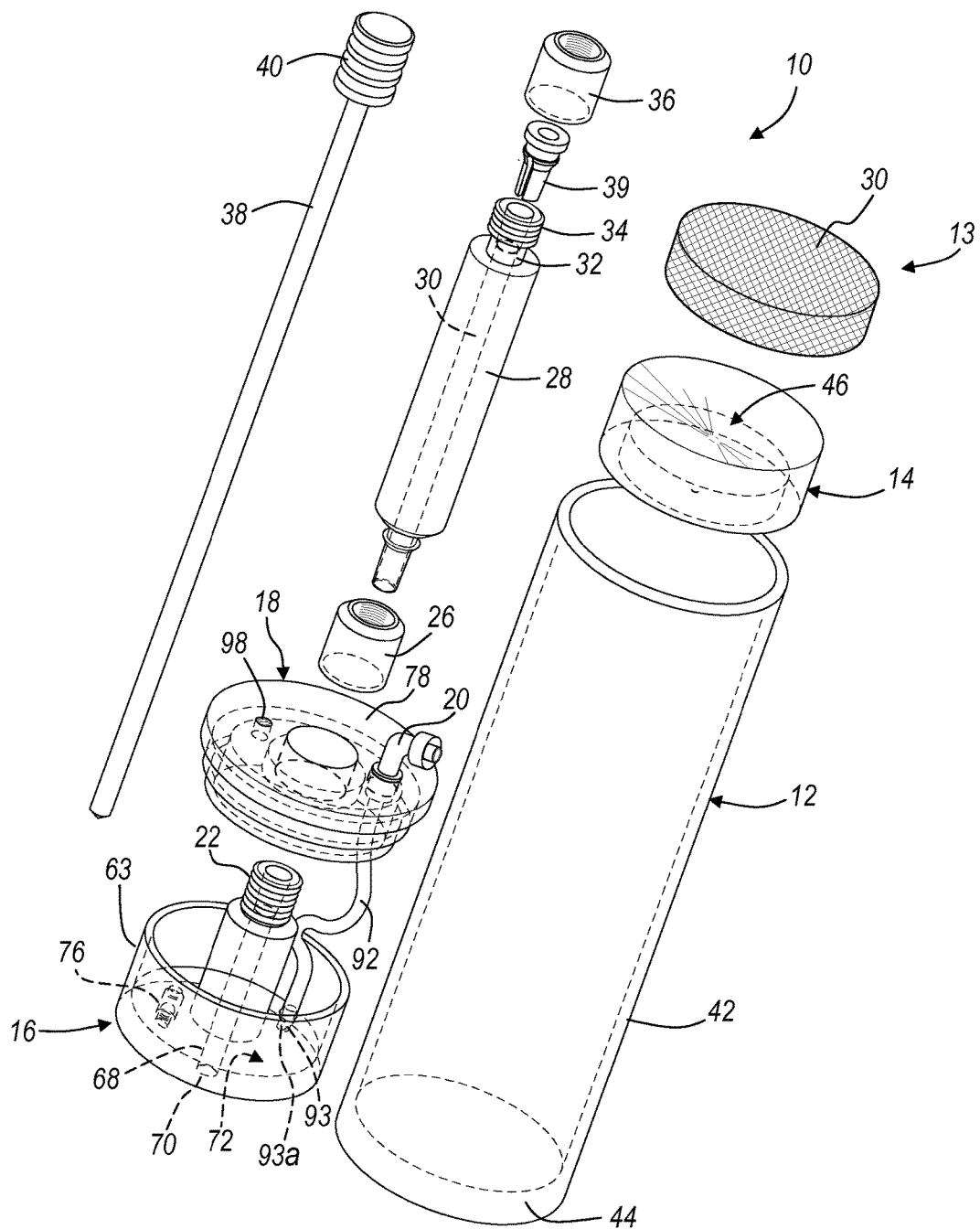
FIG. 6 is an exploded view of the separator including a plunger.

Referring to FIGS. 4-6, in a second embodiment of the present teachings a plunger is incorporated into the separator 10. The plunger 60 is also able to move within the tube 12 generally between a position closer to the open end 12*a* to a position closer to the closed end 12*b* of the tube 12.

In embodiments utilizing the piston, the cap 18 also includes a depth gage port 62. Extending from the plunger 60 and through the depth gage port 62 is a first plunger port 22. A depth guide or gage 38 includes a female connector 25 adapted to connect with the first plunger port 22. The depth gage 38 also includes a depth gage housing or cannula 28. The depth gage housing 66 defines a depth gage bore 68. Incorporated in the housing 66 and extending distal from the end mating with the plunger is a neck 70. The neck 70 includes external neck threads 72. The external neck threads 72 are adapted to engage appropriate internal threads of a mating member.

The mating member may include a compression nut 74 that mates with the external neck threads 72 to lock a depth gage rod 76 in a predetermined position. A split bushing 39 is also provided to substantially seal the depth gage housing 66 when the depth gage rod 76 is locked in place. The depth gage rod 76 extends through the depth gage housing 66 and terminates at a rod handle 78. The rod handle 78 may be a form easily manipulated by a human operator. The rod 76 extends coaxially with axis A of the tube 12. The depth gage rod 76 extends through the plunger 60 a predetermined distance and may be locked at that distance with the compression nut 74.

The plunger 60 includes a plunger front or collection face 84 and a plunger wall 80 that extends from the plunger front face 84. The plunger wall 80 extends relatively perpendicular to the plunger front face 84 and substantially parallel to the tube wall 23. Extending from the center of the plunger 60 is a sample collection projection 82. Extending from the top of the collection projection 82 is the first plunger port 22. The sample collection projection 82 includes a plunger sample collection bore 68 defined therethrough. The plunger sample collection bore 68 terminates at a sample collection aperture 86 that is substantially in the center of the plunger front face 84. The plunger front face 84 also defines an inverse cone where the sample collection aperture 86 is the apex of the cone. The plunger front face 84 defines a cone with an angle substantially similar or complimentary to the collection face 46 of the buoy 14, 300. In this way, the plunger front face 84 may mate substantially completely with the collection face 46 for reasons described more fully herein.

The plunger 60 also includes a back face 88. Extending from the plunger front face 84 to the back face 88 is a bore 74. A check valve 90 is operably connected to the bore 74. The check valve 90 allows a liquid to move from the plunger front face 84 to the back face 88 while not allowing the liquid to move from the back face 88 to the plunger front face 84. Therefore, the check valve 90 is substantially a one-way valve which allows a material to move in only one direction. The check valve 90 may also operate automatically allowing flow in only one predetermined direction. Alternatively, the check valve 90 may be operated manually and include a portion extending from the check valve 90 requiring manipulation to stop or start a flow through the check valve 90.

The plunger 60 may be made out of any appropriate material which does not interfere with the separation of the fractions of the fluid, such as whole blood. The plunger 60, however, is made of a material that is flexible or at least partially deformable. A flexible material allows the plunger 60 to have an external circumference defined by the plunger walls 63 that is substantially equal to the internal circumference of the tube 12. Because of the deformability of the plunger 60, however, the plunger 60 is still able to move within the tube 12. The plunger 60 is able to move through the tube 12 and also substantially wipe the interior of the tube wall 23. This creates, generally, a moveable seal within the tube 12. Thus, substantially no material escapes the action of the separator 10 when the plunger 60 is plunged into the tube 12. This also helps concentrate the portion of the sample desired to be collected, described more fully herein.

Formed through the center of the plate 26 is the depth gage port 62. The depth gage port 62 is also adapted to receive the sample collection projection 82. The first plunger port 22 extends above the plate 26 through the depth gage port 62. The circumference of the depth gage port 62 is substantially equal to the external circumference of the sample collection projection 82 such that a liquid seal is formed. The plate 26 defines a sample face 84 that includes an interior side of the cap 18. The area between the sample face 84 of the cap 18 and the back face 88 of the plunger 60 define a plasma collection area 92. Although the plasma collection area 92 is exemplary called the plasma collection area, it will be understood that the plasma collection area 92 may also collect any appropriate fraction of the sample that is positioned within a separator 10. The plasma collection area 92 is merely an exemplary name and an example of what material may be collected in the area of the separator 10. As discussed herein, the separator 10 may used to separate whole blood into various fractions, therefore the plasma collection area 92 is used to collect plasma. The plasma collection area 92 also allows a space for the check valve 90 to be installed.

A second bore 94 is formed in the plate 26. Extending through the second bore 94 is the fraction collection valve 20. In liquid communication with the fraction collection valve 20 is a plasma collection tube 54. The plasma collection tube 54 has a length such that the plasma collection tube 54 is able to extend from the fraction collection valve 20 to substantially the tube bottom 24. The plasma collection tube 54, however, is flexible enough such that it may be folded or compressed to fit within the plasma collection area 92 when the plunger is substantially near the top 12*a* of the tube 12. The plasma collection tube 54 may also be connected to a hose barb 93 that includes a plasma collection bore 93*a*. The plasma collection bore 93*a* is substantially level with the plunger back face 88. Alternatively, the plasma collection bore 93*a* may be positioned below the plunger back face 88 but in fluid communication with the plasma collection tube 54.

The outboard side of the fraction collection valve 20 may include external threads 94 to mate with internal threads of a plasma valve cap 96. Therefore, the fraction collection valve 20 may be selectively opened and closed via the plasma valve cap 96. It will be understood, however, that other appropriate means may be used to open and close the fraction collection valve 20 such as a clip or a plug. It will be understood that the fraction collection valve 20, plasma collection tube 54, plasma bore 23a may be used to collect any appropriate material or fraction from the separator 10.

Also formed in the plate 26 is a vent bore 98. The vent bore 98 allows air to flow into the collection area 92 as the plunger 60 is being plunged into the tube 12. The vent bore 98 may include an air filter 101 such that liquid cannot escape from the tube 12. The air filter 101 allows air to enter or escape from the collection area 92 while maintaining the liquid seal of the tube 12 produced by the cap 18.

Selectively attachable to the first plunger port 22 is the depth gage 38. The female connector 24 interconnects the depth gage housing 66 to the first plunger port 22. Internal threads in the female connector 24 mate with an external thread 103 formed on the first plunger port 22. It will be understood, however, that other engagement mechanisms between the depth gage 38 and the plunger 60 may be used. For example, a snap connection rather than a threaded connection between the two may be used.

The depth gage housing 66 is formed to be substantially rigid. Suitable materials, when sized properly, include polycarbonate and CYRO MED2®. The material preferably is both rigid and does not substantially react with the sample. It is rigid enough to provide a mechanism to plunge the plunger 60 into the tube 12. In addition the external circumference of the depth gage housing 66 is substantially equal to the circumference of the depth gage port 62 in the plate 26. Therefore, as the plunger 60 is being plunged into the tube 12 with the depth gage 38, no liquid material is allowed to escape around the depth gage housing 66 and through depth gage port 62.

Formed within the depth gage housing 66 is the bore 68 which receives the depth gage rod 76. The depth gage rod 76 extends through the sample collection bore 68 of the sample collection projection 82 and protrudes through the sample collection aperture 86 a predetermined length. The depth gage rod 76 extends through the sample collection aperture 86 a length such that when an end 105 of the depth gage rod 76 meets the buoy 14, 300, the volume defined by the collection face 46 and the plunger front face 84 is between about 5 percent and about 30 percent of the total volume of the sample that the tube 12 holds. The projection of the depth gage rod 76 allows for an easily reproducible collection amount and concentration over several trials.

The compression nut 74 locks the depth gage rod 76 in the predetermined position. Nevertheless, once the plunger 60 has been plunged to the desired depth in the tube 12, the compression nut 74 may be loosened so that the depth gage rod 76 may be removed from the plunger 60 and the depth gage housing 66 without moving the plunger 60. A syringe or other appropriate device may then be affixed to the external neck threads 72 of the depth gage 38 to extract the fraction or phase that is between the plunger front face 84 and the collection face 46. As described further herein, the fraction or phase that is left between the plunger front face 84 and the collection face 46 may be the undifferentiated cells or platelets of a bone reaming material sample. Nevertheless, it will be understood that the fraction between the plunger front face 84 and the collection face 46 may be any appropriate fraction of the sample that is disposed in the separator 10.

With reference to FIGS. 7A-7D a method using the separator 10 is illustrated. The following example relates specifically to the taking and separation of a sample of bone reaming material and whole blood from a patient. Nevertheless, it will be understood that another appropriate biological material may be separated and concentrated using the separator 10, such as adipose tissue. The bone reaming material sample may be positioned in the separator 10 and on top of the filtration system 13. As the liquid transverses the mesh 30, the separator 10 can then be used to remove unwanted macroparticles 32, such as bone chips, cartilage, etc. from the bone reaming material.

With reference to FIGS. 7A-7D and to a bone reaming material sample, a sample of bone reaming material taken from a patient is placed in the tube 12. Suitable delivery methods include spreading the material into the open end 12a of the tube using a spatula or scooping the material into the tube 12. An additional suitable delivery method includes connecting a first syringe 204 to the first plunger port 22. After which the bone reaming material sample is provided to the tube 12 via the sample collection bore 68 and sample collection aperture 86. In various embodiments, the bone reaming material is placed directly into the filtration system 13 of the tube 12. In such embodiments, the bone reaming material will filter through the mesh 30 and down towards the bottom of the tube 12b. The filtration system 13 may remain attached to the separator 10 or it may be disengaged using the break 34 prior to centrifugation. It may be advantageous to leave the filtration system 13 engaged with the tube 12 to facilitate extraction of all desired materials from the bone reaming material.

A cap 220 is then placed over the first plunger port 22 to substantially seal the tube 12. Similarly, whole blood or saline may be added to the tube to increase the viscosity of the bone reaming material. The whole blood or saline may also be introduced using the plunger port 22.

On or near collection face 46 is a third fraction 226 including a small, yet concentrated, amount of red blood cells, white blood cells, and a substantial portion of the platelets and undifferentiated cells of the bone reaming material sample. Although the undifferentiated cells are also present near the collection face 46 at this point the solid portions of the buffy coat are more compressed against the collection face 46. The position of the buoy 14, 300 also helps in this matter. Because the buoy 14, 300 is a single body it defines the interface of the plasma fraction 224 and the white/red blood cell fraction 222. Also the density of the buoy 14, 300 assures that it has not passed into the plasma fraction 224. Therefore, the fractions remain separated after the centrifuge process. In addition because the buoy 14, 300 is tuned to the density of the white/red blood cell fraction 222, it is not affected by variations in the density of the plasma fraction 224 and the position of the buoy 14 can always be at the interface of the white/red blood cell fraction 222 and the plasma fraction 224.

Figure 7A:
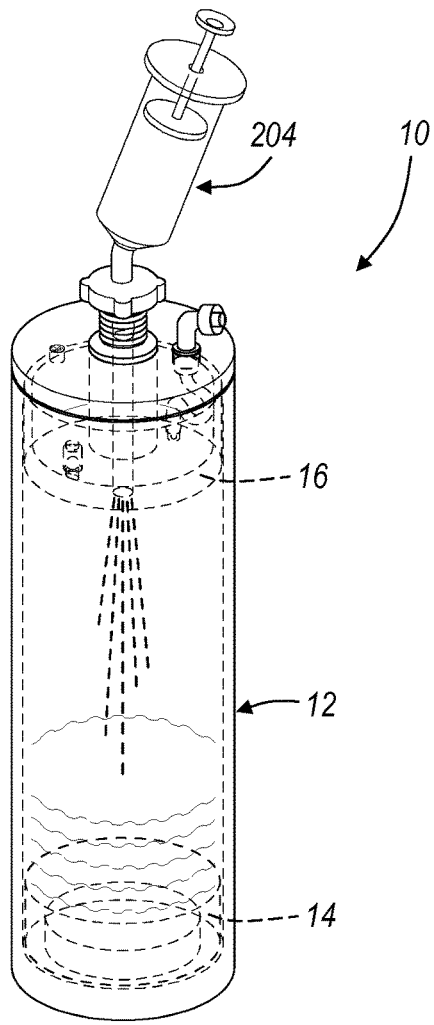
FIG. 7A is a perspective view of the separator being filled.
Figure 7B:
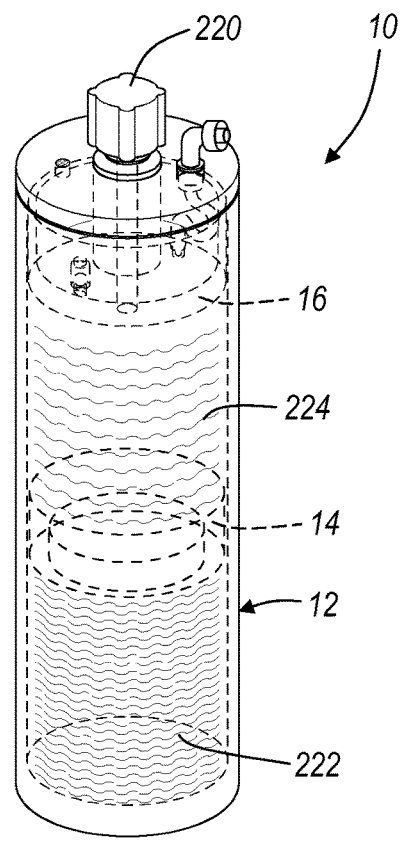
FIG. 7B is a perspective view of a sample in the separator after the centrifuge process.
Figure 7C:
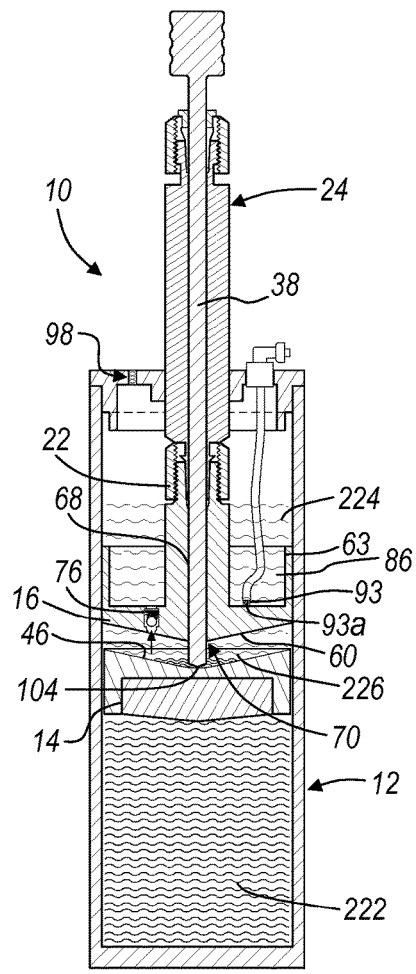
FIG. 7C is a plan view of the plunger plunged into the tube with the depth gage to further separate the bone reaming sample.

With particular reference to FIG. 7C, the depth gage 38 is affixed to the first plunger port 22 of the sample collection projection 82. After connecting the depth gage 38 to the first plunger port 22, the plunger 60 is plunged into the tube 12 by pushing on the depth gage 38. As this is performed the plasma fraction 224, formed and separated above the buoy 14, 300, is able to flow through the check valve 90 into the plasma collection area 92. This displacement of the plasma fraction 224 allows the plunger 60 to be plunged into the tube 12 containing the blood sample.

The plunger 60 is plunged into the tube 12 until the point where the end 105 of the depth gage rod 76 reaches the buoy 14, 300. The volume left in the collection face 46 is the third fraction 226 and is determined by the depth gage 38. It may be adjusted by selectively determining the amount that the depth gage rod 76 extends below the plunger front face 84. By adjusting the depth gage 38, the concentration of the third fraction 226 can be adjusted depending upon the desires of the operator.

The plasma fraction 224 is held in the plasma collection area 92 for later withdrawal. Therefore, the use of the plunger 60 and the buoy 14, 300 creates three distinct fractions that may be removed from the tube 12 after only one spin procedure. The fractions include the white/red blood cell fraction 222, held between the buoy 14, 300 and the tube bottom 24. The third or platelet or undifferentiated cell fraction 226 is held between the plunger 60 and the buoy 14, 300. Finally, the plasma fraction 224 is collected in the plasma collection area 92.

Figure 7D:
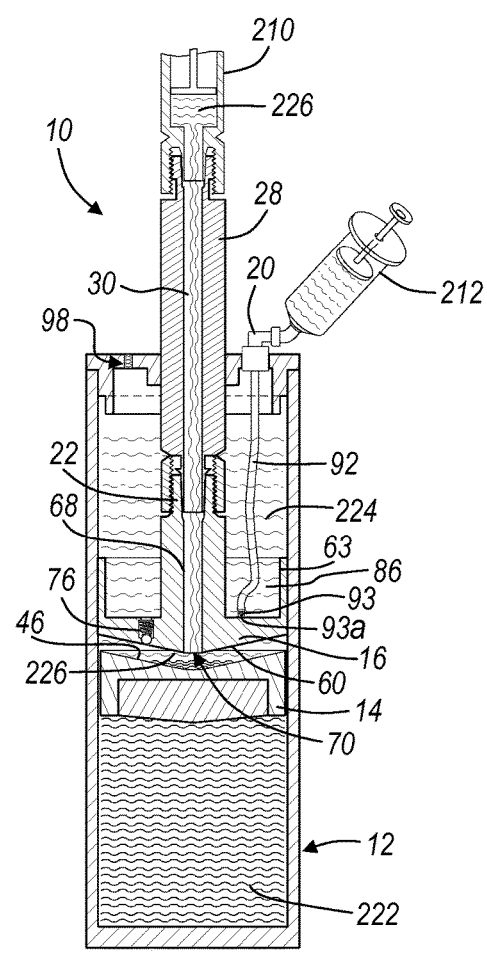
FIG. 7D is a plan view of the platelet fraction and the plasma fractions being extracted from the separator.

The third fraction 226 may be extracted from the tube 12 first, without commingling the other fractions, through the sample collection bore 68. With particular reference to FIG. 7D, the depth gage rod 76 may be removed from the depth gage housing 66. This creates a sample collection cannula which includes the depth gage bore 68, the sample collection bore 68, and the sample collection aperture 86. After the depth gage rod 76 has been removed, the second syringe 210 may be affixed to the depth gage housing 66 via the external neck threads 72. The second syringe 210 may be substantially similar to the first syringe 204.

Before attempting to withdraw the third fraction 226, the separator 10 may be agitated to re-suspend the platelets and concentrated white/red blood cells in a portion of the plasma remaining in the collection face 46. This allows for easier and more complete removal of the third fraction 226 because it is suspended rather than compressed against the collection face 46. A vacuum is then created in the second syringe 210 by pulling back the plunger to draw the third fraction 226 into the second syringe 210.

As the third fraction 226 is drawn into the second syringe 210 the plunger 60 moves towards the buoy 14, 300. This action is allowed because of the vent bore 98 formed in the cap 18. Atmospheric air is transferred to the plasma collection area 92 through the vent bore 98 to allow the third fraction 226 to be removed. This allows the movement of the plunger 60 towards the buoy 14, 300. This action also allows the plunger 60 to "wipe" the collection face 46. As the plunger front face 84 mates with the collection area 46 the third fraction 226 is pushed into the sample collection aperture 86. This ensures that substantially the entire third fraction 226 collected in the collection area 46 is removed into the second syringe 210. It can also increase the repeatability of the collection volumes. In addition, because the second syringe 210 does not protrude out the sample collection aperture 86, it does not interfere with the collection of the third fraction 226. Once the plunger front face 84 has mated with the collection face 46 there is substantially no volume between the plunger 60 and the buoy 14, 300.

Once the third fraction 226 is extracted the second syringe 210 is removed from the first plunger port 22. Also the extraction of the third fraction 226 leaves the plasma fraction 224 and the red blood cell fractions 222 separated in the tube 12. At this point a third syringe 212 may be affixed to the fraction collection valve 20. The third syringe 212 is connected to the external threads 94 of the fraction collection valve 20 to ensure a liquid tight connection. It will be understood, however, that another connection mechanism such as a snap or compression engagement may be used to connect the third syringe 212 to the fraction collection valve 20.

A vacuum is then created in the third syringe 212 to draw the plasma fraction 224 from the plasma collection area 92 through the plasma collection tube 54. As discussed above, the plasma collection tube 54 is connected to the hose barb 93. Therefore, the plasma flows through the plasma collection bore 93a through the hose barb 93, and then through the plasma collection tube 54. It will be understood that the plasma collection tube 54 may alternatively simply rest on the plunger back face 88 to collect the plasma fraction 224. In this way the plasma fraction 224 may be removed from the separator 10 without commingling it with the white/red blood cell fraction 222. After the plasma fraction 224 is removed, the separator 10 may be dismantled to remove the white/red blood cell fraction 222. Alternatively, the separator 10 may be discarded in an appropriate manner while retaining the white/red blood cell fraction 222.

The separator 10 allows for the collection of three components of a bone reaming material and whole blood sample's fractions with only one centrifugation spin. The interaction of the buoy 14, 300 and the plunger 60 allows a collection of about 40% to nearly 100% of the available buffy coat in the whole blood sample portion of the mixture after a centrifuge processing time of about 5 minutes to about 15 minutes. The complimentary geometry of the plunger front face 84 and the collection face 46 help increase the collection efficiency. Although only the cone geometry is discussed herein, it will be understood that various other geometries may be used with similar results.

The plunger front face 84 being flexible also helps ensure a complete mating with the collection face 46. This, in turn, helps ensure that substantially the entire volume between the two is evacuated. The process first begins with the suction withdrawal of the third fraction 226 via the second syringe 210, but is completed with a fluid force action of the third fraction 226 as the plunger front face 84 mates with the collection face 46. As the plunger front face 84 mates with the collection face 46 the fluid force assists in removal of the selected fraction.

The plunger 60 also substantially wipes the tube wall 23. Because the plunger 60 is formed of a flexible material it forms a seal with the tube wall 23 which is movable. Therefore, substantially no liquid is able to move between the plunger wall 80 and the tube wall 23. Material is substantially only able to go past the plunger front face 84 via the check valve 90.

The complimentary geometry also helps decrease the collection time of the third fraction 226. Therefore, entire time to prepare and remove the third fraction 226 is generally about 5 to about 40 minutes. This efficiency is also assisted by the fact that the separator 10 allows for the removal of the third fraction 226 without first removing the plasma fraction 224, which includes the buffy coat, and respinning the plasma fraction 224. Rather one spin in the separator 10 with the whole blood sample allows for the separation of the buffy coat for easy extraction through the plunger 60.

Figure 8:
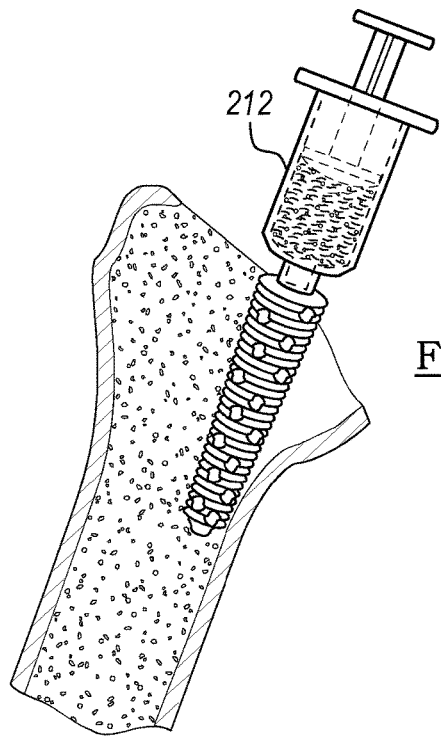
FIG. 8 depicts the removal of bone reaming material from a subject.
Figure 9:
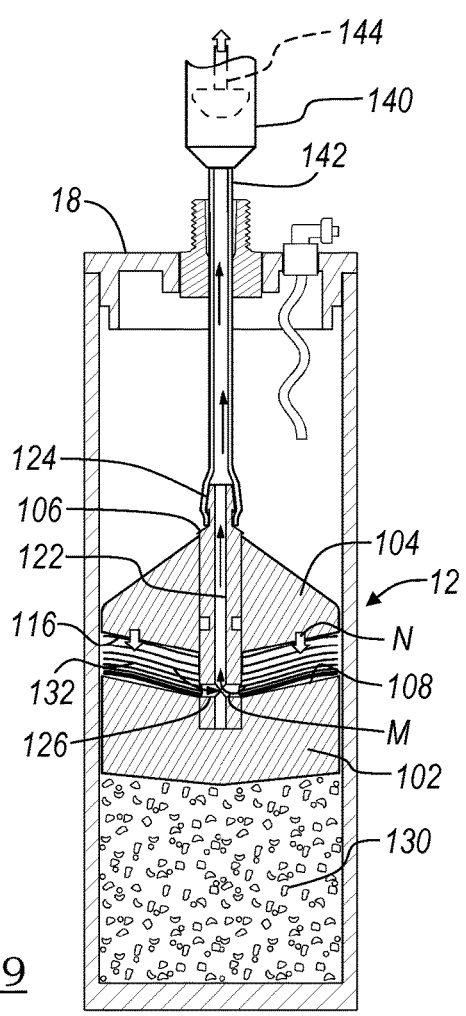
FIG. 9 illustrates a plan view of a selected fraction of the separated material being extracted from a tube according to various embodiments.

The separator 10 may be used to separate any appropriate material. The material may be separated for any purpose, such as a surgical procedure. For example, a selected fraction of a whole heterogeneous material or multi-component material may be separated and purified into a desired fraction according to various embodiments. The multi-component material can be harvested from a patient by methods such as bone reaming, as depicted in FIG. 8, or by withdrawing whole blood from the patient. The selected fraction of the bone reaming material may include various components, such as undifferentiated cells. The various undifferentiated cells may be positioned in a selected scaffold or relative to a selected portion of a patient for providing a volume of the undifferentiated cells to the patient. The selected fraction is applied to or delivered to the patient at a selected region of the anatomy. The selected fraction may be placed on a prosthetic, a stent, or any other implantable medical device. The selected fraction may be applied directly to the anatomy or to the medical implant in any appropriate manner, such as by spraying, dipping, infiltrating, or any appropriate method. The macroparticles 32 recovered can also be used to fill a void in bone.

The description of the teachings is merely exemplary in nature and, thus, variations that do not depart from the gist of the teachings are intended to be within the scope of the teachings. Such variations are not to be regarded as a departure from the spirit and scope of the teachings.

The invention claimed is:

1. A method of separating a component of a multiple component material, comprising:
    separating, within a container system, at least a portion of a solid portion from a liquid portion of a multicomponent material at least by retaining the portion of the solid portion of the multiple component material in a first section of the container system with a filtration system having a first filter media portion positioned between the first section and a second section of the container system, wherein a buoy is slidably received within the second section, the buoy having a first buoy member and a second buoy member;
    forming at least a first fraction and a second fraction of the liquid portion after the liquid portion has moved from the first section to the second section, wherein the buoy moves within the second section to isolate the first fraction at least from the second fraction;
    removing the first section from the second section following fractionation such that the first filter media portion is removed from the second section, wherein the first filter media portion retains the portion of the solid portion of the multiple component material in the first section during fractionation; and
    extracting the first fraction from the second section.

2. The method of claim 1, further comprising:
    sizing the first section and the second section to have the same transverse cross-section dimensions.

3. The method of claim 1, further comprising:
    providing the first section to include the first filter media portion and a second filter media portion.

4. The method of claim 1, further comprising:
    obtaining a volume of the multiple component material from an anatomy, the volume comprising the solid and liquid portions; and
    placing the obtained volume of the multiple component material in the container system having at least the first section and the second section.

5. The method of claim 4, wherein providing the volume of the multiple component material comprises a selected volume of bone reaming material.

6. The method of claim 1, wherein forming at least the first fraction and the second fraction of the liquid portion includes applying a force to the container system to form at least the first fraction and the second fraction.

7. The method of claim 6, wherein applying the force includes centrifuging the container system to move the buoy to a selected position relative to the volume of a fraction of a whole heterogeneous material.

8. The method of claim 1, further comprising:
    at least one of applying the first fraction to an implantable medical device, applying the first fraction to a wound, applying the first fraction to a reamed bone, applying the first fraction to a resected bone, or combinations thereof.

9. The method of claim 1, further comprising a connecting member connecting the first buoy member and the second buoy member, at least the second buoy member being slidably coupled to the connecting member, such that the second buoy member is movable relative to the first buoy member.

10. The method of claim 1, wherein the first fraction is disposed between the first and second buoy members, and the step of extracting the first fraction from the second section comprises applying suction to a port disposed between the first and second buoys to draw the first fraction into the port and through a cannula in fluid communication with an exterior of the container system.

11. A method of separating a component of a multiple component material, comprising:
    placing a volume of the multiple component material, including a liquid portion and a solid portion, in a removable filter section of a container, the container having at least the filter section and a fractionation section, wherein a buoy is slidably received within the fractionation section, the buoy having a first buoy member and a second buoy member;
    separating the solid portion from the liquid portion at least by retaining at least a portion of the solid portion of the multiple component material in the filter section of the container;
    forming a fraction of the liquid portion in the fractionation section of the container, wherein the buoy moves within the fractionation section to isolate the fraction of the liquid portion;
    maintaining a connection of the filter section and the fractionation section while forming the fraction of the liquid portion in the fractionation section of the container, wherein the filter section retains the portion of the solid portion of the multiple component material; and
    extracting the fraction from the fractionation section of the container.

12. The method of claim 11, wherein the filter section and the fractionation section have the same cross-sectional dimensions for connecting the filter and fractionation sections.

13. The method of claim 11, further comprising:
    removably connecting a first section to the fractionation section.

14. The method of claim 11, wherein forming the fraction includes:
    applying a force to the multiple component material supported in the filter section.

15. The method of claim 14, wherein the force is applied to at least cause a portion of the liquid portion to move into the fractionation section of the container.

16. The method of claim 14, wherein forming the fraction of the liquid portion includes collecting at least the fraction between the first buoy member and the second buoy member positioned within the fractionation section.

17. The method of claim 11, further comprising a connecting member connecting the first buoy member and the second buoy member, at least the second buoy member being slidably coupled to the connecting member, such that the second buoy member is movable relative to the first buoy member.

18. A method of separating a component of a multiple component material, comprising:
  providing a container system for separating at least a first portion of a solid portion from a liquid portion of a multiple component material at least by retaining the first portion of the solid portion of the multiple component material in a first section of the container system with a filtration system having a first filter media portion positioned between the first section and a second section of the container system;
  after the liquid portion has moved from the first section to the second section, providing a fractionation system to form at least one fraction of the liquid portion between a first buoy member and a second buoy member, wherein the first filter media portion retains the first portion of the solid portion of the multiple component material during forming of the at least one fraction of the liquid portion; and
  providing access within the second section to extract the at least one fraction of the liquid portion from the second section from between the first buoy member and the second buoy member;
  wherein the first section is removably coupled to the second section.

19. The method of claim 18, wherein the first buoy member and the second buoy member are complementary formed to substantially mate during extracting the at least one fraction of the liquid portion.

20. The method of claim 18, further comprising:
  providing the solid material to include bone portions and the liquid portion to include whole blood.

21. The method of claim 18, further comprising:
  providing the first section to be removed from the second section following a separation of at least the solid portion from the liquid portion and prior to a forming of the at least one fraction.

22. The method of claim 18, further comprising a connecting member connecting the first buoy member and the second buoy member, at least the second buoy member being slidably coupled to the connecting member, such that the second buoy member is movable relative to the first buoy member.

23. The method of claim 18, further comprising extracting the at least one fraction of the liquid portion from the second section by applying suction to a port disposed between the first and second buoys to draw the at least one fraction of the liquid portion into the port and through a cannula in fluid communication with an exterior of the container system.

* * * * *